(12) United States Patent
Norwood et al.

(10) Patent No.: US 7,932,482 B2
(45) Date of Patent: Apr. 26, 2011

(54) DIFFUSER WITH LIGHT EMITTING DIODE NIGHTLIGHT

(75) Inventors: Richard L. Norwood, Racine, WI (US); Jose Porchia, Greenfield, WI (US); Jeffrey J. Wolf, Racine, WI (US); Imre J. Dancs, Greenfield, WI (US); Edward L. Paas, Los Altos, CA (US); Scott D. Walter, Twin Lakes, WI (US); George J. Dietz, Delafield, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 1386 days.

(21) Appl. No.: 10/544,548

(22) PCT Filed: Feb. 9, 2004

(86) PCT No.: PCT/US2004/003533
§ 371 (c)(1),
(2), (4) Date: May 10, 2006

(87) PCT Pub. No.: WO2004/071935
PCT Pub. Date: Aug. 26, 2004

(65) Prior Publication Data
US 2006/0237439 A1    Oct. 26, 2006

(30) Foreign Application Priority Data
May 13, 2003  (WO) .................. PCT/US03/14769

(51) Int. Cl.
*H05B 1/02* (2006.01)

(52) U.S. Cl. ........ 219/506; 219/502; 219/494; 392/390; 362/96

(58) Field of Classification Search .................. 219/497, 219/492, 501, 502, 505; 392/390; 362/96, 362/86, 101, 102; 261/142
See application file for complete search history.

(56) References Cited

U.S. PATENT DOCUMENTS

| 38,150 A | 4/1863 | Colburn |
| 446,953 A | 2/1891 | Robert |

(Continued)

FOREIGN PATENT DOCUMENTS

| DE | 3609511 | 10/1986 |

(Continued)

OTHER PUBLICATIONS

European Search Report, Appl. No. EP 04709400.8, dated Oct. 4, 2006.

*Primary Examiner* — Mark H Paschall

(57) ABSTRACT

An electrically operated diffuser has a fragrance-emitting element (8) for facilitating diffusion of an active material, and at least one light emitting diode (7). The at least one light emitting diode (7) serves as a nightlight and has a luminous intensity rating of at least about 5000 mcd at 20 mA. Also, the at least one light emitting diode (7) may be positioned at a back surface of the diffuser, such that when an active material is received in the compartment the at least one light emitting diode (7) shines through the active material. The diffuser may include a remote-use assembly to supply power to the diffuser from a wall socket remote from the diffuser. The diffuser may also include a light controller to change one or more of the color and the intensity of the at least one light emitting diode (7).

52 Claims, 16 Drawing Sheets

U.S. PATENT DOCUMENTS

| | | | |
|---|---|---|---|
| 514,422 A | 2/1894 | Kellogg |
| 554,115 A | 2/1896 | Fisher |
| 699,652 A | 5/1902 | Campbell et al. |
| 1,178,575 A | 4/1916 | Collins |
| 1,403,548 A | 1/1922 | Gudeman |
| 1,712,204 A | 5/1929 | Gibney |
| 1,751,257 A | 3/1930 | Vallebuona et al. |
| 1,800,156 A | 4/1931 | Rotheim |
| 1,977,997 A | 10/1934 | Patterson et al. |
| 1,981,650 A | 11/1934 | Larsen |
| 1,994,932 A | 3/1935 | Vidal |
| 2,192,019 A | 2/1940 | Schepmoes |
| 2,230,265 A | 2/1941 | Robinson |
| 2,372,371 A | 3/1945 | Eisner |
| 2,424,268 A | 7/1947 | Delane et al. |
| 2,435,756 A | 2/1948 | Schlesinger |
| 2,469,656 A | 5/1949 | Lienert |
| 2,557,501 A | 6/1951 | Fusay et al. |
| 2,591,818 A | 4/1952 | Huff |
| 2,597,195 A | 5/1952 | Smith |
| 2,668,993 A | 2/1954 | Bair |
| 2,931,880 A | 4/1960 | Yaffe |
| 2,942,090 A | 6/1960 | Diehl |
| 3,248,530 A | 4/1966 | Titmas |
| 3,358,552 A | 12/1967 | Schneider |
| 3,373,341 A | 3/1968 | Wattson |
| 3,386,005 A | 5/1968 | Roland et al. |
| 3,436,310 A | 4/1969 | Arnold et al. |
| 3,443,083 A | 5/1969 | Curran |
| 3,543,122 A | 11/1970 | Klebanoff et al. |
| 3,545,650 A | 12/1970 | Williams |
| 3,588,859 A | 6/1971 | Petree |
| 3,615,041 A | 10/1971 | Bischoff |
| 3,747,902 A | 7/1973 | Bailey |
| 3,780,260 A | 12/1973 | Elsner |
| 3,790,772 A | 2/1974 | Newman et al. |
| 3,864,080 A | 2/1975 | Valbona et al. |
| 3,872,280 A | 3/1975 | Van Dalen |
| 3,948,445 A | 4/1976 | Andeweg |
| 4,084,079 A | 4/1978 | Costello |
| 4,106,671 A | 8/1978 | Sharples |
| 4,166,293 A | 9/1979 | Anis |
| 4,184,612 A | 1/1980 | Freyre |
| 4,197,671 A | 4/1980 | De Brouwer |
| 4,202,387 A | 5/1980 | Upton |
| 4,217,315 A | 8/1980 | Keeler, II |
| 4,229,415 A | 10/1980 | Bryson |
| 4,244,525 A | 1/1981 | Manna |
| 4,250,537 A | 2/1981 | Roegner et al. |
| 4,285,028 A | 8/1981 | Sundin et al. |
| 4,301,095 A | 11/1981 | Mettler et al. |
| 4,315,665 A | 2/1982 | Haines |
| 4,338,547 A | 7/1982 | McCaslin |
| 4,346,059 A | 8/1982 | Spector |
| 4,391,781 A | 7/1983 | van Lit |
| 4,415,797 A | 11/1983 | Choustoulakis |
| 4,432,938 A | 2/1984 | Meetze, Jr. |
| 4,435,732 A | 3/1984 | Hyatt |
| 4,493,011 A | 1/1985 | Spector |
| 4,549,250 A | 10/1985 | Spector |
| 4,571,485 A | 2/1986 | Spector |
| 4,583,686 A | 4/1986 | Martens et al. |
| 4,597,781 A | 7/1986 | Spector |
| 4,609,978 A | 9/1986 | Hsieh et al. |
| 4,611,266 A | 9/1986 | Schwartz |
| 4,666,638 A | 5/1987 | Baker et al. |
| 4,670,820 A | 6/1987 | Eddins et al. |
| 4,689,515 A | 8/1987 | Benndorf et al. |
| 4,702,418 A | 10/1987 | Carter et al. |
| 4,703,155 A | 10/1987 | Suhajda |
| 4,703,314 A | 10/1987 | Spani |
| 4,707,338 A | 11/1987 | Spector |
| 4,714,984 A | 12/1987 | Spector |
| 4,715,702 A | 12/1987 | Dillon |
| 4,739,928 A | 4/1988 | O'Neil |
| 4,750,471 A | 6/1988 | Hautmann et al. |
| 4,785,642 A | 11/1988 | Chin et al. ................ 63/1.1 |
| 4,795,883 A | 1/1989 | Glucksman et al. |
| 4,816,973 A | 3/1989 | Atalla et al. |
| 4,830,791 A | 5/1989 | Muderlak et al. |
| 4,837,421 A | 6/1989 | Luthy |
| 4,840,444 A | 6/1989 | Hewitt |
| 4,844,050 A | 7/1989 | Hautmann et al. |
| 4,849,606 A | 7/1989 | Martens, III et al. |
| 4,856,103 A | 8/1989 | Compton |
| 4,858,079 A | 8/1989 | Ohashi |
| 4,866,580 A | 9/1989 | Blackerby |
| 4,870,551 A | 9/1989 | Nagel |
| 4,873,029 A | 10/1989 | Blum |
| 4,934,792 A | 6/1990 | Tovi |
| 4,955,714 A | 9/1990 | Stotler et al. |
| 4,968,487 A | 11/1990 | Yamamoto et al. |
| 5,017,909 A | 5/1991 | Goekler |
| 5,038,394 A | 8/1991 | Hasegawa et al. |
| 5,055,822 A | 10/1991 | Campbell et al. |
| 5,095,647 A | 3/1992 | Zobele et al. |
| 5,111,477 A | 5/1992 | Muderlak |
| 5,115,975 A | 5/1992 | Shilling |
| 5,118,319 A | 6/1992 | Smith et al. |
| 5,135,485 A | 8/1992 | Cohen et al. |
| 5,136,483 A | 8/1992 | Schoniger et al. |
| 5,147,585 A | 9/1992 | Blum |
| 5,175,791 A * | 12/1992 | Muderlak et al. ............. 392/390 |
| 5,201,025 A | 4/1993 | Landesberg |
| 5,213,523 A | 5/1993 | Hygema et al. |
| 5,214,458 A | 5/1993 | Kanai |
| 5,222,186 A | 6/1993 | Schimanski et al. |
| 5,230,837 A | 7/1993 | Babasade |
| 5,233,375 A | 8/1993 | Williams et al. |
| 5,260,919 A | 11/1993 | Tsai |
| 5,274,215 A | 12/1993 | Jackson |
| 5,283,601 A | 2/1994 | Lowe |
| 5,283,723 A | 2/1994 | Wu |
| 5,309,185 A | 5/1994 | Harper |
| 5,309,338 A | 5/1994 | Liu |
| 5,324,490 A | 6/1994 | Van Vlahakis |
| D350,209 S | 8/1994 | Martin |
| 5,370,829 A | 12/1994 | Kunze |
| 5,382,410 A | 1/1995 | Peltier |
| D357,330 S | 4/1995 | Wong et al. |
| 5,419,879 A | 5/1995 | Vlahakis et al. |
| 5,432,623 A | 7/1995 | Egan et al. |
| 5,449,117 A | 9/1995 | Muderlak et al. |
| 5,452,270 A | 9/1995 | Ikeda et al. |
| 5,464,710 A | 11/1995 | Yang |
| 5,483,689 A | 1/1996 | O'Donnell, Jr. et al. |
| 5,484,086 A | 1/1996 | Pu |
| 5,485,308 A | 1/1996 | Hirata et al. |
| 5,497,102 A | 3/1996 | Burrows et al. |
| 5,498,397 A | 3/1996 | Horng |
| 5,512,371 A | 4/1996 | Gupta et al. |
| 5,517,264 A | 5/1996 | Sutton |
| 5,521,357 A | 5/1996 | Lock et al. |
| 5,524,101 A | 6/1996 | Thorgersen et al. |
| D372,769 S | 8/1996 | Ganor |
| 5,544,812 A | 8/1996 | Torres |
| 5,549,247 A | 8/1996 | Rossman et al. |
| 5,556,192 A | 9/1996 | Wang |
| 5,591,409 A | 1/1997 | Watkins |
| 5,616,172 A | 4/1997 | Tuckerman et al. |
| 5,633,623 A | 5/1997 | Campman |
| D381,443 S | 7/1997 | Yuen |
| D381,444 S | 7/1997 | Yuen |
| 5,647,053 A | 7/1997 | Schroeder et al. |
| 5,662,835 A | 9/1997 | Collingwood |
| 5,673,825 A | 10/1997 | Chen |
| 5,690,509 A | 11/1997 | Eisenbraun |
| D386,974 S | 12/1997 | Wefler |
| 5,716,119 A | 2/1998 | Patel |
| D393,063 S | 3/1998 | Wefler |
| 5,752,766 A | 5/1998 | Bailey et al. |
| 5,757,111 A | 5/1998 | Sato |
| 5,757,459 A | 5/1998 | Bhalakia et al. |
| D395,529 S | 6/1998 | Yuen |
| 5,763,080 A | 6/1998 | Stahl et al. |
| 5,772,074 A | 6/1998 | Dial et al. |
| 5,788,931 A | 8/1998 | Munoz Quintana |

| Patent No. | Date | Name |
|---|---|---|
| 5,830,578 A | 11/1998 | Ono et al. |
| 5,852,946 A | 12/1998 | Cowger |
| 5,863,108 A | 1/1999 | Lederer |
| 5,871,153 A | 2/1999 | Doggett, Jr. |
| 5,875,968 A | 3/1999 | Miller et al. |
| 5,876,678 A | 3/1999 | Harrell et al. |
| 5,882,256 A | 3/1999 | Shropshire .................... 454/157 |
| 5,903,710 A | 5/1999 | Wefler et al. |
| 5,909,845 A | 6/1999 | Greatbatch et al. |
| 5,922,231 A | 7/1999 | Karst et al. |
| 5,924,784 A | 7/1999 | Chliwnyj et al. |
| D412,569 S | 8/1999 | Muller |
| 5,937,140 A | 8/1999 | Leonard et al. |
| 5,940,577 A | 8/1999 | Steinel |
| 5,945,094 A | 8/1999 | Martin et al. |
| 5,964,519 A | 10/1999 | Chun-Ying |
| 5,976,503 A | 11/1999 | Martin et al. |
| 5,980,064 A | 11/1999 | Metroyanis |
| 6,016,038 A | 1/2000 | Mueller et al. |
| 6,020,983 A | 2/2000 | Neu et al. |
| 6,039,899 A | 3/2000 | Martin et al. |
| 6,044,202 A | 3/2000 | Junkel |
| 6,057,527 A | 5/2000 | Kilmer |
| 6,072,606 A | 6/2000 | Huether et al. |
| 6,097,881 A | 8/2000 | DeWitt et al. |
| 6,101,038 A | 8/2000 | Hebert et al. |
| 6,104,866 A | 8/2000 | DeWitt et al. |
| 6,104,867 A | 8/2000 | Stathakis et al. |
| 6,123,935 A | 9/2000 | Wefler et al. |
| 6,127,656 A | 10/2000 | Kilmer |
| 6,135,369 A | 10/2000 | Prendergast et al. |
| D433,521 S | 11/2000 | Jaworski |
| D433,744 S | 11/2000 | Basaganas |
| 6,142,653 A | 11/2000 | Larson |
| 6,145,241 A | 11/2000 | Okuno |
| 6,149,283 A | 11/2000 | Conway et al. |
| 6,150,943 A | 11/2000 | Lehman et al. |
| 6,151,827 A | 11/2000 | Smith et al. |
| 6,153,703 A | 11/2000 | Lustiger et al. |
| 6,154,607 A | 11/2000 | Flashinski et al. |
| D434,842 S | 12/2000 | Thomas et al. |
| 6,163,098 A | 12/2000 | Taylor et al. |
| 6,166,496 A | 12/2000 | Lys et al. |
| D436,657 S | 1/2001 | Heatter |
| D437,069 S | 1/2001 | Allison |
| D437,636 S | 2/2001 | Basaganas |
| 6,191,826 B1 | 2/2001 | Murakami et al. |
| 6,196,471 B1 | 3/2001 | Ruthenberg |
| 6,199,983 B1 | 3/2001 | Kato et al. |
| 6,216,925 B1 | 4/2001 | Garon |
| 6,236,807 B1 | 5/2001 | Ruffolo et al. |
| 6,239,216 B1 | 5/2001 | Montanari et al. |
| 6,241,362 B1 | 6/2001 | Morrison |
| 6,254,065 B1 | 7/2001 | Ehrensperger et al. |
| 6,267,297 B1 | 7/2001 | Contadini et al. |
| 6,268,062 B1 | 7/2001 | Demeuse |
| 6,270,720 B1 | 8/2001 | Mandish |
| 6,275,651 B1 | 8/2001 | Voit |
| 6,278,840 B1 | 8/2001 | Basaganas Millan |
| 6,281,867 B2 | 8/2001 | Kurematsu |
| 6,292,196 B1 | 9/2001 | Fukunaga et al. |
| 6,292,305 B1 | 9/2001 | Sakuma et al. |
| 6,302,559 B1 | 10/2001 | Warren |
| 6,337,080 B1 | 1/2002 | Fryan et al. |
| 6,341,732 B1 | 1/2002 | Martin et al. |
| D453,562 S | 2/2002 | Makino |
| 6,350,417 B1 | 2/2002 | Lau et al. |
| 6,361,192 B1 | 3/2002 | Fussell et al. |
| 6,361,752 B1 | 3/2002 | Demarest et al. |
| D455,486 S | 4/2002 | Makino |
| 6,368,564 B1 | 4/2002 | Smith |
| 6,377,164 B1 | 4/2002 | Fulmer |
| 6,390,453 B1 | 5/2002 | Frederickson et al. |
| 6,392,549 B1 | 5/2002 | Wu |
| 6,398,381 B1 | 6/2002 | Tseng |
| D460,544 S | 7/2002 | Garcia |
| D460,573 S | 7/2002 | Gee, II |
| 6,420,877 B1 | 7/2002 | Replogle |
| 6,423,892 B1 | 7/2002 | Ramaswamy |
| D461,549 S | 8/2002 | Garcia |
| D461,885 S | 8/2002 | Jordi |
| 6,431,719 B1 | 8/2002 | Lau et al. |
| 6,439,471 B2 | 8/2002 | Ehrlich et al. |
| D462,755 S | 9/2002 | Millan |
| 6,446,880 B1 | 9/2002 | Schram et al. |
| D464,416 S | 10/2002 | von Dohlen et al. |
| 6,457,826 B1 | 10/2002 | Lett |
| 6,466,739 B2 | 10/2002 | Ambrosi et al. |
| 6,478,440 B1 * | 11/2002 | Jaworski et al. ................. 362/96 |
| 6,479,594 B1 | 11/2002 | Cheung et al. |
| 6,482,863 B2 | 11/2002 | Munagavalasa et al. |
| D468,033 S | 12/2002 | Warren et al. |
| 6,503,459 B1 | 1/2003 | Leonard et al. |
| D469,862 S | 2/2003 | Cruver, IV et al. |
| 6,536,746 B2 | 3/2003 | Watkins |
| D473,638 S | 4/2003 | Cruver, IV |
| 6,547,553 B2 | 4/2003 | Koch et al. |
| 6,554,203 B2 | 4/2003 | Hess et al. |
| 6,557,998 B2 | 5/2003 | Portney |
| 6,558,022 B2 | 5/2003 | Kawahara |
| 6,567,613 B2 | 5/2003 | Rymer |
| 6,569,387 B1 | 5/2003 | Furner et al. |
| D475,446 S | 6/2003 | Millan |
| 6,575,610 B2 | 6/2003 | Natsume |
| 6,577,072 B2 | 6/2003 | Saito |
| 6,581,915 B2 | 6/2003 | Bartsch et al. |
| 6,584,986 B2 | 7/2003 | Gindl |
| 6,588,435 B1 | 7/2003 | Gindl |
| 6,602,475 B1 | 8/2003 | Chiao |
| 6,606,548 B2 | 8/2003 | Kato et al. |
| 6,611,297 B1 | 8/2003 | Akashi et al. |
| 6,619,559 B2 | 9/2003 | Wohrle et al. |
| 6,622,662 B1 | 9/2003 | Wolpert et al. |
| D480,792 S | 10/2003 | Millan |
| 6,631,888 B1 | 10/2003 | Prueter |
| D481,787 S | 11/2003 | Millan |
| 6,644,507 B2 | 11/2003 | Borut et al. |
| D483,104 S | 12/2003 | Hill et al. |
| 6,661,967 B2 | 12/2003 | Levine et al. |
| 6,667,576 B1 | 12/2003 | Westhoff |
| 6,676,284 B1 | 1/2004 | Wynne Willson |
| 6,682,331 B1 | 1/2004 | Peh et al. |
| 6,685,339 B2 | 2/2004 | Daughtry et al. |
| 6,685,343 B2 | 2/2004 | Mabuchi |
| 6,688,752 B2 | 2/2004 | Moore |
| 6,690,120 B2 | 2/2004 | Oskorep et al. |
| 6,697,571 B2 | 2/2004 | Triplett et al. |
| 6,698,665 B2 | 3/2004 | Minamite et al. |
| 6,713,024 B1 | 3/2004 | Arnell et al. |
| 6,714,725 B2 | 3/2004 | Grone et al. |
| 6,719,217 B1 | 4/2004 | Tawara et al. |
| 6,721,102 B2 | 4/2004 | Bourdelais et al. |
| 6,727,332 B2 | 4/2004 | Demain |
| 6,729,552 B1 | 5/2004 | McEwen |
| 6,729,746 B2 | 5/2004 | Suehiro et al. |
| 6,733,719 B2 | 5/2004 | DiNardo et al. |
| 6,733,898 B2 | 5/2004 | Kim et al. |
| 6,752,327 B2 | 6/2004 | Martens, III et al. |
| 6,758,566 B2 | 7/2004 | Goulden et al. |
| 6,759,961 B2 | 7/2004 | Fitzgerald et al. |
| 6,763,624 B2 | 7/2004 | Gow |
| 6,766,773 B2 | 7/2004 | Wolpert et al. |
| 6,768,865 B2 | 7/2004 | Stathakis et al. |
| 6,775,470 B2 | 8/2004 | Zobele et al. |
| 6,779,905 B1 * | 8/2004 | Mazursky et al. ............. 362/101 |
| 6,782,194 B2 | 8/2004 | Schneiderbauer |
| 6,783,117 B2 | 8/2004 | Wohrle |
| 6,788,011 B2 | 9/2004 | Mueller et al. |
| 6,792,199 B2 | 9/2004 | Levine et al. |
| 6,801,003 B2 | 10/2004 | Schanberger et al. |
| 6,802,460 B2 | 10/2004 | Hess et al. |
| 6,806,659 B1 | 10/2004 | Mueller et al. |
| 6,810,204 B2 | 10/2004 | Grone et al. |
| 6,811,287 B2 | 11/2004 | Roller et al. |
| 6,813,094 B2 | 11/2004 | Kaminsky et al. |
| 6,819,506 B1 | 11/2004 | Taylor et al. |
| 6,824,296 B2 | 11/2004 | Souza et al. |
| 6,827,286 B2 | 12/2004 | Zobele |

| Patent/Pub No. | Date | Name |
|---|---|---|
| 6,827,466 B2 | 12/2004 | Tsai |
| 6,829,852 B1 | 12/2004 | Uehran |
| 6,832,794 B2 | 12/2004 | He et al. |
| 6,837,585 B2 | 1/2005 | Roggatz |
| 6,839,506 B2 | 1/2005 | He et al. |
| 6,843,965 B2 | 1/2005 | Matulevich |
| 6,843,969 B1 | 1/2005 | Anno |
| 6,846,098 B2 | 1/2005 | Bourdelais et al. |
| 6,848,795 B2 | 2/2005 | Kaminsky et al. |
| 6,850,697 B2 | 2/2005 | Basaganas Millan |
| 6,854,717 B2 | 2/2005 | Millan |
| 6,857,579 B2 | 2/2005 | Harris |
| D502,540 S | 3/2005 | Cruver, IV et al. |
| 6,864,110 B2 | 3/2005 | Summers et al. |
| 6,871,794 B2 | 3/2005 | McEwen |
| 6,871,982 B2 | 3/2005 | Holman et al. |
| D504,171 S | 4/2005 | Ibarra et al. |
| 6,885,811 B2 | 4/2005 | He et al. |
| 6,889,003 B2 | 5/2005 | Triplett et al. |
| 6,890,642 B2 | 5/2005 | Kaminsky et al. |
| 6,895,177 B2 | 5/2005 | He et al. |
| 6,897,381 B2 | 5/2005 | He et al. |
| 6,899,280 B2 | 5/2005 | Kotary et al. |
| 6,901,215 B2 | 5/2005 | He et al. |
| 6,901,925 B2 | 6/2005 | Coughlin |
| 6,909,840 B2 | 6/2005 | Harwig et al. |
| 6,917,754 B2 | 7/2005 | Pedrotti et al. |
| 6,920,282 B2 | 7/2005 | He et al. |
| D508,558 S | 8/2005 | Wolpert et al. |
| 6,923,383 B1 | 8/2005 | Joshi |
| 6,924,233 B1 | 8/2005 | Chua et al. |
| 6,926,435 B2 | 8/2005 | Li |
| 6,931,202 B2 | 8/2005 | Pedrotti et al. |
| 6,933,680 B2 | 8/2005 | Oskorep et al. |
| 6,938,883 B2 | 9/2005 | Adams et al. |
| 6,945,468 B1 | 9/2005 | Rodriguez et al. |
| 6,946,805 B2 | 9/2005 | Segan et al. |
| 6,950,607 B2 | 9/2005 | Yip et al. |
| 6,953,260 B1 | 10/2005 | Allen |
| 6,953,265 B2 | 10/2005 | Suehiro et al. |
| 6,955,581 B1 | 10/2005 | Liu |
| 6,957,012 B2 | 10/2005 | He et al. |
| 2001/0011779 A1 | 8/2001 | Stover |
| 2001/0032655 A1 | 10/2001 | Gindi |
| 2002/0021892 A1 | 2/2002 | Ambrosi et al. |
| 2002/0036617 A1 | 3/2002 | Pryor |
| 2002/0048169 A1 | 4/2002 | Dowling et al. |
| 2002/0066798 A1 | 6/2002 | Laudamiel-Pellet et al. |
| 2002/0068009 A1 | 6/2002 | Laudamiel-Pellet et al. |
| 2002/0068010 A1 | 6/2002 | Laudamiel-Pellet et al. |
| 2002/0075677 A1 | 6/2002 | Dokoupil |
| 2002/0097978 A1 | 7/2002 | Lowry et al. |
| 2002/0113912 A1 | 8/2002 | Wright et al. |
| 2002/0136542 A1 | 9/2002 | He et al. |
| 2002/0136886 A1 | 9/2002 | He et al. |
| 2002/0145394 A1 | 10/2002 | Morgan et al. |
| 2002/0159274 A1 | 10/2002 | Hubbell et al. |
| 2002/0172512 A1 | 11/2002 | Stathakis et al. |
| 2002/0195975 A1 | 12/2002 | Schanberger et al. |
| 2003/0012018 A1 | 1/2003 | Kluth |
| 2003/0028260 A1 | 2/2003 | Blackwell |
| 2003/0028888 A1 | 2/2003 | Hunter et al. |
| 2003/0035917 A1 | 2/2003 | Hyman |
| 2003/0057887 A1 | 3/2003 | Dowling et al. |
| 2003/0063902 A1 | 4/2003 | Pedrotti et al. |
| 2003/0076281 A1 | 4/2003 | Morgan |
| 2003/0137258 A1 | 7/2003 | Piepgras et al. |
| 2003/0138241 A1 | 7/2003 | Pedrotti et al. |
| 2003/0147243 A1 | 8/2003 | Alduby |
| 2003/0168524 A1 | 9/2003 | Hess et al. |
| 2003/0168751 A1 | 9/2003 | Bartsch et al. |
| 2003/0169400 A1 | 9/2003 | Buazza et al. |
| 2003/0169513 A1 | 9/2003 | Kaminsky et al. |
| 2003/0169514 A1 | 9/2003 | Bourdelais et al. |
| 2003/0175019 A1 | 9/2003 | Bresolin et al. |
| 2003/0175148 A1 | 9/2003 | Kvietok et al. |
| 2003/0194355 A1 | 10/2003 | Pedrotti et al. |
| 2003/0205364 A1 | 11/2003 | Sauciuc et al. |
| 2003/0206411 A9 | 11/2003 | Dowling et al. |
| 2003/0214080 A1 | 11/2003 | Maki et al. |
| 2004/0004839 A1 | 1/2004 | Souza et al. |
| 2004/0007710 A1 | 1/2004 | Roy et al. |
| 2004/0007787 A1 | 1/2004 | Kvietok et al. |
| 2004/0009103 A1 | 1/2004 | Westring |
| 2004/0016818 A1 | 1/2004 | Murdell et al. |
| 2004/0028551 A1 | 2/2004 | Kvietok et al. |
| 2004/0033067 A1 | 2/2004 | He et al. |
| 2004/0033171 A1 | 2/2004 | Kvietok et al. |
| 2004/0035409 A1 | 2/2004 | Harwig et al. |
| 2004/0044106 A1 | 3/2004 | Portnoy et al. |
| 2004/0076410 A1 | 4/2004 | Zobele et al. |
| 2004/0095746 A1 | 5/2004 | Murphy |
| 2004/0105264 A1 | 6/2004 | Spero |
| 2004/0105669 A1 | 6/2004 | He et al. |
| 2004/0124988 A1 | 7/2004 | Leonard et al. ............... 340/612 |
| 2004/0131509 A1 | 7/2004 | He et al. |
| 2004/0141315 A1 | 7/2004 | Sherburne |
| 2004/0144884 A1 | 7/2004 | He et al. |
| 2004/0145067 A1 | 7/2004 | Millan |
| 2004/0150994 A1 | 8/2004 | Kazar et al. |
| 2004/0160199 A1 | 8/2004 | Morgan et al. |
| 2004/0179167 A1 | 9/2004 | Dahi et al. |
| 2004/0208675 A1 | 10/2004 | Horikoshi et al. |
| 2004/0247300 A1 | 12/2004 | He et al. |
| 2004/0249094 A1 | 12/2004 | Demain |
| 2005/0024868 A1 | 2/2005 | Nagai et al. |
| 2005/0029688 A1 | 2/2005 | Hagmann et al. |
| 2005/0035728 A1 | 2/2005 | Schanberger et al. |
| 2005/0053368 A1 | 3/2005 | Pesu et al. |
| 2005/0053528 A1 | 3/2005 | Rymer |
| 2005/0063194 A1 | 3/2005 | Lys et al. |
| 2005/0068777 A1 | 3/2005 | Popovic |
| 2005/0069304 A1 | 3/2005 | He et al. |
| 2005/0069306 A1 | 3/2005 | He et al. |
| 2005/0069307 A1 | 3/2005 | He et al. |
| 2005/0105186 A1 | 5/2005 | Kaminsky et al. |
| 2005/0105296 A1 | 5/2005 | French |
| 2005/0105303 A1 | 5/2005 | Emde |
| 2005/0117365 A1 | 6/2005 | Menke |
| 2005/0122065 A1 | 6/2005 | Young |
| 2005/0122292 A1 | 6/2005 | Schmitz et al. |
| 2005/0122721 A1 | 6/2005 | Hori |
| 2005/0122722 A1 | 6/2005 | Menke |
| 2005/0128743 A1 | 6/2005 | Chuey et al. |
| 2005/0133617 A1 | 6/2005 | Hidalgo et al. |
| 2005/0146893 A1 | 7/2005 | Ford et al. |
| 2005/0147523 A1 | 7/2005 | Laudamiel-Pellet et al. |
| 2005/0147539 A1* | 7/2005 | Laudamiel-Pellet et al. . 422/120 |
| 2005/0157499 A1 | 7/2005 | Kim |
| 2005/0167522 A1 | 8/2005 | Wheatley et al. |
| 2005/0168986 A1 | 8/2005 | Wegner |
| 2005/0174777 A1 | 8/2005 | Cooper et al. |
| 2005/0178345 A1 | 8/2005 | Crapser |
| 2005/0180736 A1 | 8/2005 | Zobele |
| 2005/0185392 A1 | 8/2005 | Walter et al. |
| 2005/0185395 A1 | 8/2005 | Pinter |
| 2005/0191481 A1 | 9/2005 | He et al. |
| 2005/0194460 A1 | 9/2005 | Selander |
| 2005/0195598 A1 | 9/2005 | Dancs et al. |
| 2005/0196159 A1 | 9/2005 | Zobele |
| 2005/0201107 A1 | 9/2005 | Seki |
| 2005/0201944 A1 | 9/2005 | Kvietok et al. |
| 2005/0205916 A1 | 9/2005 | Conway et al. |
| 2005/0211790 A1 | 9/2005 | Kvietok et al. |
| 2005/0212404 A1 | 9/2005 | Chen et al. |
| 2005/0214158 A1 | 9/2005 | Kvietok et al. |
| 2005/0218243 A1 | 10/2005 | Zobele et al. |
| 2005/0219838 A1 | 10/2005 | Belliveau |
| 2005/0225856 A1 | 10/2005 | Kokuzawa et al. |
| 2005/0226788 A1 | 10/2005 | Hrybyk et al. |
| 2005/0232831 A1 | 10/2005 | Taylor et al. |
| 2006/0193611 A1 | 8/2006 | Ballesteros et al. |
| 2006/0231213 A1 | 10/2006 | Matsuda et al. |

FOREIGN PATENT DOCUMENTS

| | | |
|---|---|---|
| DE | 3701499 | 7/1988 |
| DE | 4131613 | 3/1993 |
| DE | 4446413 | 12/1994 |

| | | | | | | |
|---|---|---|---|---|---|---|
| EP | 0 252 642 | 1/1988 | | JP | 07-009744 | 2/1995 |
| EP | 0537130 B1 | 4/1993 | | JP | 7230847 | 8/1995 |
| EP | 0548274 B1 | 6/1993 | | JP | 08-084551 | 4/1996 |
| EP | 0617667 A1 | 10/1994 | | JP | 08-241039 | 9/1996 |
| EP | 0705281 A1 | 4/1996 | | JP | 8278413 | 10/1996 |
| EP | 0736248 A1 | 10/1996 | | JP | 09-074971 | 3/1997 |
| EP | 0945062 B1 | 9/1999 | | JP | 9107861 | 4/1997 |
| EP | 0956868 B1 | 11/1999 | | JP | 308422 | 12/1997 |
| EP | 1 033 139 | 9/2000 | | JP | 10014467 | 1/1998 |
| EP | 1 219 308 | 7/2002 | | JP | 10057464 | 3/1998 |
| EP | 1332765 A1 | 8/2003 | | JP | 2004057548 | 2/2004 |
| EP | 1422249 A1 | 5/2004 | | JP | 2004275371 | 10/2004 |
| ES | 1005422 | 11/1988 | | WO | WO 91/15249 | 10/1991 |
| ES | 1015255 | 6/1991 | | WO | WO 96/04021 | 2/1996 |
| GB | 2277267 A | 10/1994 | | WO | WO 97/13539 | 4/1997 |
| GB | 2369816 A | 6/2002 | | WO | WO 98/19526 | 5/1998 |
| JP | 54-21247 | 2/1979 | | WO | WO 98/58692 | 12/1998 |
| JP | 62094169 | 4/1987 | | WO | 0145470 A1 | 6/2001 |
| JP | 1295808 | 11/1989 | | WO | WO 01/43785 A1 | 6/2001 |
| JP | 2078077 | 3/1990 | | WO | 0168154 A1 | 9/2001 |
| JP | 2138577 | 5/1990 | | WO | WO 01/79752 | 10/2001 |
| JP | 2242633 | 9/1990 | | WO | WO 02/09772 | 2/2002 |
| JP | 3240701 | 10/1991 | | WO | WO 03/095334 | 11/2003 |
| JP | 5003744 | 1/1993 | | WO | WO 03098971 A1 | 11/2003 |
| JP | 6003627 | 1/1994 | | WO | WO 2004071935 A2 | 8/2004 |
| JP | 06-36643 | 5/1994 | | WO | WO 2005/030276 | 4/2005 |
| JP | 6155489 | 6/1994 | | WO | WO 2005/092400 | 10/2005 |
| JP | 6205929 | 7/1994 | | | | |
| JP | 06-262057 | 9/1994 | | | | |

* cited by examiner

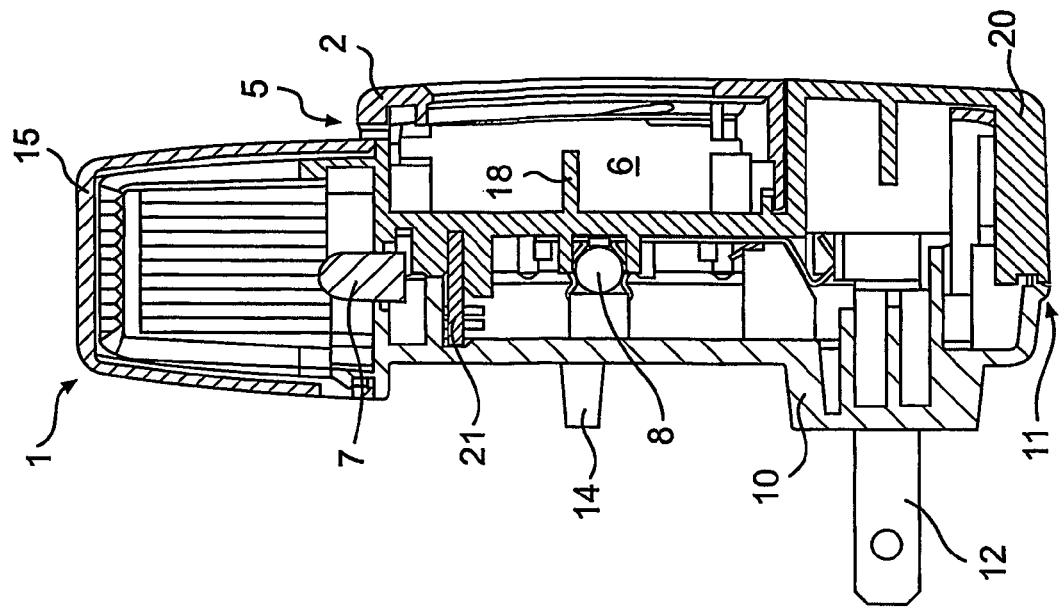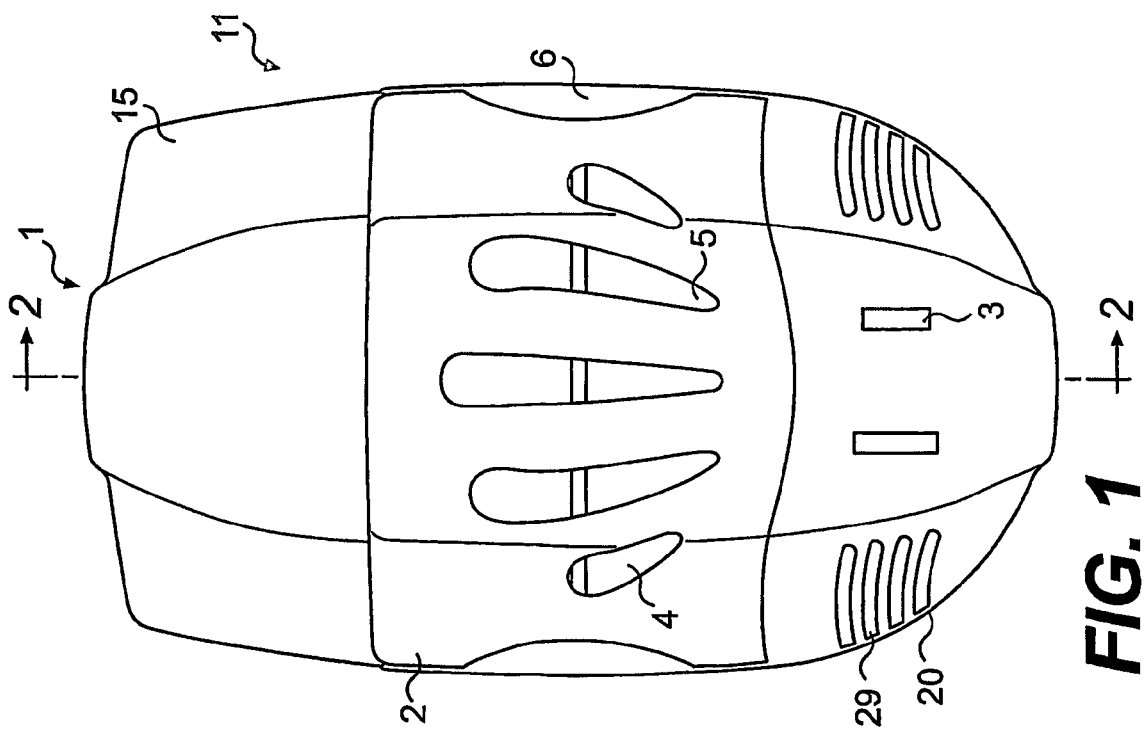

DIFFUSER WITH LIGHT EMITTING DIODE NIGHTLIGHT

FIELD OF THE INVENTION

Our invention generally relates to plug-in diffusers, having one or more LEDs used as nightlights and/or ornamental displays.

BACKGROUND OF THE INVENTION

Plug-in diffusers are known in the art. Such diffusers are plugged directly into wall sockets and generate heat to facilitate the diffusion of an active material, such as air freshener or insect control material. Such diffusers are also known as heat-assisted evaporative dispensers. One particular type of plug-in diffuser employs a liquid or gel air-treating composition in an enclosure, all or part of which is formed of a polymeric film. When heated, the air-treating composition can migrate through the polymeric film to be released as a vapor at an outer surface. The use of this type of permeable polymeric membrane controls the dispensing of air-treating vapors, and tends to eliminate great variations in rate of dispensing over the life of the product. Another conventional type of plug-in diffuser employs a liquid air freshener, such as scented oil, contained in a clear plastic container or bottle. A plug-in scented oil diffuser is described in, for example, U.S. Pat. No. 5,647,053.

Various types of fragrance dispensers, other than the evaporative type, are also known in the art. With respect to the many devices known for dispensing fragrance, U.S. Pat. No. 5,382,410 discloses an electrostatic vapor/aerosol generator for supplying aromatic oil, deodorant, disinfectant, fumigant, fungicide, insecticide or bactericide to a room. U.S. Pat. No. 4,702,418 discloses an adjustable aerosol dispenser for supplying different amounts of a fragrance into a room according to sensed light, odor, sound, etc., within the room. U.S. Pat. No. 5,115,975 discloses a device for emitting a vaporized substance into the atmosphere according to the setting of a timer. U.S. Pat. No. 6,135,369 discloses an electrostatic sprayer which can spray insecticides, which can be controlled according to selected on times and off times, and which incorporates a sensor to sense the available power for continued operation. U.S. Pat. No. 4,689,515 discloses an ultrasonic liquid atomizer with automatic frequency control. U.S. Pat. Nos. 3,543,122 and 3,615,041 disclose aerosol dispensers having timers for controlling the operation of the dispensers according to preset times.

Also, additional dispensers of the type often referred to as plug-in diffusers are described in U.S. Pat. Nos. 4,849,606, 5,937,140, and 6,478,440, which are assigned to S.C. Johnson & Son, Inc., of Racine, Wis. In particular, it is noted that U.S. Pat. No. 6,478,440 ("the '440 patent"), which is incorporated herein by reference, discloses a fragrance warmer incorporating plug-through capability and an incandescent nightlight. The combination of incandescent bulbs and fragrance dispensers in plug-in devices has proven popular.

Incandescent nightlights, however, suffer from various disadvantages. For example, incandescent bulbs produce considerable heat. When incandescent nightlights are used in connection with a diffuser of volatile active material, the heat generated by the incandescent nightlight tends to affect the rate at which the active material is diffused. Thus, when the nightlight is turned on, the active material may, for example, be diffused too quickly. Also, because of the added heat, it is difficult to regulate the rate at which an active material is diffused.

Another disadvantage of using incandescent bulbs as nightlights is that they tend to consume relatively large amounts of energy. Since nightlights are often left on for extended periods of time in multiple rooms of a house, this energy consumption can be a significant consideration.

Various techniques, such as using different incandescent bulbs and using bulbs of varying size or power rating, have been tried in order to reduce the heat produced and the power consumed by nightlights. These techniques, however, have yielded only mild reductions in heat emission and energy consumption, and come at a cost to performance of the nightlight.

Recently, several documents have suggested reducing the power consumption of a nightlight by using a light emitting diode (LED) as the light source of the nightlight. For example, U.S. Patent Application Publication No. 2002/0075677 discloses a nightlight using a number of LEDs as the light source, arranged in series with a current-limiting capacitor.

In addition, lighting devices which emit different colored light, such as from LEDs are generally known, as demonstrated with respect to the use of multiple LEDs in a single unit, as disclosed in U.S. Pat. No. 6,149,283.

Furthermore, U.S. patent application Ser. No. 10/212,746, assigned to S.C. Johnson & Son, Inc., which was filed on Dec. 5, 2002, discloses a liquid vaporizer including a nightlight, wherein the nightlight may be an incandescent lamp, a neon lamp, or an LED device. None of the foregoing documents, however, describes a preferred combination of a plug-in diffuser and a low-temperature, low-power nightlight, which provides sufficient light, is long lasting, is inexpensive to manufacture, and is easy to use, in the manner of our invention.

Another problem with conventional plug-in diffusers is that they do not make effective use of lighting elements. For example, lighting elements in conventional diffusers are typically not used to generate aesthetic lighting displays, such as multicolored displays, color-changing displays, projection displays, shine-through displays, or the like.

A still further problem is that conventional plug-in diffusers are limited in their use to locations where wall sockets are already exist. Wall sockets are often located in places that are less than ideal for placement of diffusers, such as near the floor, in a corner, etc. This limitation on the location of plug-in diffusers is even more problematic for diffusers that have a lighting element or display, since the diffuser often cannot be located in a user's line of sight, thereby limiting the effectiveness of the lighting element.

Yet another problem is that conventional diffusers typically do not have suitable controllability for varying the emission of light and/or fragrance. In particular, such plug-in diffusers seldom include fragrance dispensers that are easily and precisely adjustable to vary a fragrance intensity or diffusion rate, such as, for example, piezoelectric fragrance dispensing pumps.

Thus, a need exists in the art for a plug-in diffuser that resolves these and other problems in the prior art.

SUMMARY OF THE INVENTION

Plug-in diffusers according to our invention include at least one LED, which can be used as a low-temperature, low-power nightlight, and/or ornamental displays. The one or more LEDs can also preferably be provided in combination with other sensory stimulation, such as fragrance and/or sound.

More specifically, in one aspect, our invention relates to an electrically operated diffuser, comprising a housing, a plug, a heating element, and at least one LED. The housing has a compartment formed therein for receiving an active material. The plug is disposed on the housing for connection of the diffuser to a power source, such as, for example, a wall socket. The heating element is located in proximity to the compartment of the housing, to heat an active material received in the compartment. The at least one LED is disposed in the housing and serves as a nightlight. The heating element and the LED are electrically connected to the plug. Preferably, the at least one LED comprises a plurality of LEDs of at least two different colors. The diffuser may preferably comprise a light controller for controlling the operation of the plurality of light emitting diodes and a processor for controlling the operation of the light controller.

The at least one light emitting diode may preferably be positioned at a back surface of the compartment of said housing, such that when the active material is received in the compartment said at least one light emitting diode "shines through" the active material. With this embodiment, the active material is preferably a liquid active material, such as translucent scented oil, contained in a transparent or translucent container so that substantial light can shine through. This embodiment is, however, also applicable to diffusers using gel cartridges, or other materials that are somewhat less transmissive to light.

The diffuser may also preferably comprise a remote-use assembly so that the diffuser can be used at locations other than a wall socket. In such a preferred embodiment, the remote-use assembly includes a support member that supports the diffuser on a support surface remote from the wall socket, and a cord that supplies power to the plug of the diffuser from the wall socket.

In another aspect, our invention relates to an electrically operated diffuser, comprising a housing, a plug, a resistance heater, and at least one LED. The housing has a compartment formed therein for receiving an active material. The plug is disposed on the housing for connection of the diffuser to a power source. The resistance heater is located in proximity to the compartment of the housing, to heat an active material received in the compartment. The at least one LED is disposed in the housing and serves as a nightlight, the LED preferably having a luminous intensity rating of at least about 5000 millicandela (mcd) at 20 mA. The heating element and the LED are electrically connected to the plug, the at least one LED preferably being electrically connected to the plug via a full-wave bridge circuit. When activated, the at least one LED preferably provides minimal heat to an active material received in the compartment of said housing. As used herein the term "minimal heat" means that the heat generated by the LED(s) is negligible when compared to the heat generated by the heating element(s). For example, in a device having a single LED and a single heating element, an LED that generate less than about 5% of the heat generated by the heating element would be considered to generate minimal heat. Of course, in devices having plural LEDs or LED arrays, the heat generated by the LEDs may exceed 5% and still be considered minimal.

In still another aspect, our invention relates to an electrically operated diffuser comprising a housing, a plug, a heating element, at least one light emitting diode, and a remote-use assembly. The housing has a compartment for receiving an active material. The plug is disposed on the housing for connection of the diffuser to a power source. The heating element is located in proximity to the compartment of the housing, to heat an active material received in the compartment. The at least one light emitting diode is disposed in the housing and serves as a light. The heating element and the at least one light emitting diode are electrically connected to said plug. The at least one light emitting diode is positioned at a back surface of the compartment of the housing, such that when the active material is received in the compartment the at least one light emitting diode shines through the active material. The remote-use assembly comprises a support member that supports the diffuser on a support surface remote from the wall socket, and a cord that supplies power to the plug of the diffuser from the wall socket.

In yet another aspect, our invention relates to an electrically operated diffuser comprising a housing, a heating element, and at least one light emitting diode. The housing includes a compartment for receiving an active material. The heating element is located in proximity to the compartment of the housing, to heat an active material received in the compartment. The at least one light emitting diode is disposed in the housing and shines through at least one window in the housing to project an image in the shape of the at least one window.

In addition, the remote-use assembly of our invention can be used with any suitable diffuser, including conventional diffusers, to allow the diffuser to be used in locations remote from a wall socket. The remote-use assembly comprises a support member that supports the diffuser on a support surface remote from the wall socket, and a cord that supplies power to the plug of the diffuser from the wall socket.

In one preferable variation, the remote-use assembly may preferably include a docking station that releasably holds the diffuser during use. The cord of the remote-use assembly transmits electrical energy from the wall socket to said docking station to power the diffuser. The docking station preferably comprises a cradle for receiving and supporting the diffuser during use, and an electrical receptacle electrically connected to the cord, for receiving the plug of the diffuser and supplying power to the diffuser from the cord. Preferably, the remote-use assembly further comprises a transformer/rectifier for converting alternating current from the wall socket to direct current; the cord transmitting the direct current to the receptacle to power the diffuser.

In another preferable variation, the remote-use assembly may be configured with a direct-corded arrangement. In this variation, the diffuser preferably comprises a support member comprising a base formed integrally with the housing of the diffuser to support the diffuser on the support surface remote from the wall socket. Preferably, the remote-use assembly of this variation further comprises a transformer/rectifier for converting alternating current from the wall socket to direct current, and a receptacle electrically connected to the cord of the remote-use assembly; the receptacle being adapted to receive the plug of the diffuser.

Of course, there is no requirement that the diffuser be separable from the remote-use assembly. Accordingly, a diffuser according to our invention may preferably be provided with a cord fixedly attached to the diffuser to supply energy to the diffuser from a remote wall socket. In this variation, the cord is not removable from the diffuser. Accordingly, the diffuser is preferably provided with a base coupled with the housing of the diffuser to support the diffuser on the support surface remote from the wall socket.

Both of the remote-use assembly variations described can be adapted to be used with the various diffusers according to our invention as well as various conventional diffusers.

A better understanding of these and other aspects, features, and advantages of our invention may be had by reference to the drawings and to the accompanying description, in which preferred embodiments of the invention are illustrated and described.

BRIEF DESCRIPTION OF THE DRAWINGS

FIG. 1 is a front view of a preferred embodiment of the plug-in diffuser of our invention, showing the housing and external components of our invention.

FIG. 2 is a cross-sectional side view of the plug-in diffuser of FIG. 1, taken along the line 2-2.

DETAILED DESCRIPTION OF THE PREFERRED EMBODIMENTS

Figure 4:
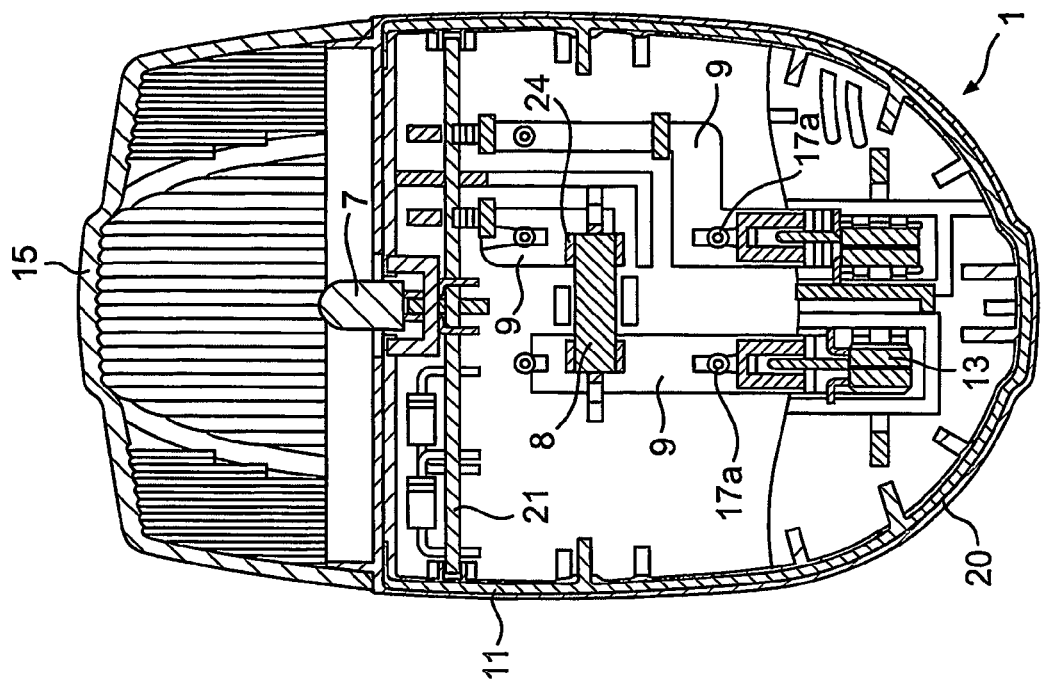
FIG. 4 is a cross-sectional view of the plug-in diffuser of FIG. 1, taken along line 4-4 in FIG. 3.

Our invention generally relates to plug-in diffusers having a low-temperature, low-power nightlight, that provides sufficient light for use as a nightlight, is long lasting, is inexpensive to manufacture, and is easy to use. In addition, diffusers according to our invention may include one or more of (i) a "shine-through" feature wherein light from a lighting element such as an LED shines through a container of active material such as a bottle of scented oil fragrance, (ii) a "remote-use" arrangement wherein a remote-use assembly supplies power to the diffuser from a remote wall socket, and (iii) a "display feature" wherein the emission of light, fragrance, and/or sound is controlled by a user, preferably, in a coordinated manner. It should be understood that any of the features and elements described herein could be used alone or in various combinations with each other. Several preferred embodiments and combinations are discussed in detail below.

Diffuser with LED Nightlight

A preferred plug-in diffuser according to our invention generally comprises a housing 11, a compartment or slot 6 for receiving an active material, a heating element 8, and a lighting element 7. The housing 11 and its various components are described in detail below with reference to FIGS. 1-5.

The heating element 8 is preferably a coil resistance heater, a wire-wound resistor, an encapsulated wire-wound resistor, or a metal oxide resistance heater, for example. If a metal oxide resistor is used, it may preferably be potted in a ceramic block. Other alternative heating units that may be used include PTC (Positive Temperature Coefficient) heaters, printed ink circuitry, and etched foil heating devices. Other known heating devices may also be used taking into account cost, reliability, and convenience of packaging for manufacture.

Instead of a heating element, our invention may alternatively use a pumping device to facilitate the diffusion of an active material by pumping out a small portion of an active material fluid. A diffuser/atomizer having a piezoelectric atomizing pump is described in U.S. Pat. No. 6,450,419. One of ordinary skill in the art would readily understand that such a piezoelectric device could be incorporated with the nightlight element of our invention. Also, a fan-assisted device may be used, either alone or in combination with one of the above devices, to facilitate the emission of fragrance.

The lighting element 7 of our invention may be a single LED or a plurality of LEDs, such as one or more LED arrays. If multiple LEDs are used, they may be arranged in, for example, a line, a circle, a square, a flower shape, a rainbow shape, or any other desired shape or arrangement. Our invention may employ LEDs of the same or different colors depending on the particular aesthetic design of the diffuser. For example, a red and/or green LED could be used during the holidays. In one preferred aspect, the LED lighting element 7 of our invention provides sufficient light, i.e., is of a sufficient luminous intensity, to satisfactorily perform as a nightlight. That is, the lighting element 7 is not a low intensity on/off indicator light, a warning light, or the like, that typically has a nominal luminous intensity on the order of a few hundred millicandela (mcd). The LED lighting element 7 of our invention serves as a light and preferably has a nominal luminous intensity of at least 1300 mcd at 20 milliamps (mA), and more preferably at least 5000 mcd at 20 mA. It may also be suitable to use multiple LED lighting elements, each having a luminous intensity lower than 1300 mcd. The LED lighting element of our invention preferably has an average lifetime of at least one year or approximately 8700 hours. Alternatively, or in combination with the LED nightlight 7, the diffuser may include one or more LED arrays, which could be controlled independently or together, to provide an ornamental design.

In one particularly preferred embodiment of our invention, a single, white, LED having a viewing angle of at least 30°, a nominal or typical luminous intensity of between about 5000 and about 6000 mcd at 20 mA is used. Further, the lighting element 7 of this particular embodiment preferably has an expected lifetime of at least 10,000 hours, and most preferably at least 20,000 hours.

The LED lighting element 7 used with our invention produces a much whiter light than an incandescent bulb used in conventional nightlights. In addition, the LED lighting element 7 is much more robust and durable than an incandescent bulb, in part because there is no filament that could break.

This is advantageous from the manufacturing, assembly, and shipping standpoints, since fewer of the lighting elements will be damaged during production and shipping, thereby decreasing costs. The LED lighting elements also tend to have a longer life than incandescent bulbs having comparable luminous intensities.

Furthermore, the LED lighting element 7 of our invention uses substantially less power than conventional nightlight devices. The total power consumption of the diffuser 1, i.e., the combined power consumption of the heating element 8 and the LED lighting element 7, is preferably less than two watts. Of the power consumed by the diffuser 1 as a whole, only a small fraction (less than 0.1 watt) is used to power the LED lighting element 7. This minimal power consumption by the LED lighting element 7 means that the LED lighting element 7 emits very little heat. The small amount of heat that is emitted by the LED lighting element 7 is negligible compared to the heat generated by the heating element 8. Therefore, the activation of the LED lighting element 7 supplies minimal heat to the active material, and consequently has little affect on the diffusion rate thereof. This allows the diffusion rate of the active material to be effectively regulated to a more precise degree than was previously possible with active material diffusers having an incandescent nightlight. Other embodiments of our invention that require more heat to diffuse the active material, such as insect control diffusers and scented oil diffusers, may consume more power. For example, insect control diffusers having an LED lighting element 7 according to our invention may consume around five watts, and the scented oil diffusers may consume as much as 3.7 watts. However, even in these higher power applications, the LED lighting element 7, preferably, is still only consuming a small portion (about 0.1 watts) of the total power consumed by the diffuser. The heating element in each of these cases consumes substantially all of the power.

FIG. 1 illustrates a frontal view of a thermal diffuser 1, showing decorative features as well as functional aspects of the invention. The housing or external surface 11 of the dispenser or thermal diffuser 1 may be of any acceptable material, such as a moldable plastic material or a hard synthetic rubber composition. Due to cost considerations and ease of manufacture, preferred materials include polypropylene, nylon, and the like. The housing 11 constitutes the outer shell of the diffuser, and is comprised of a number of subassemblies that clip or fit snugly together during assembly, preferably permanently, so as to prevent the consumer from accidentally damaging, or gaining access to the electrical circuitry contained within. Such subassemblies may be glued or cemented together by known adhesives, or may be of such close tolerance fit as to prevent easy disassembly. These subassemblies, which are illustrated in greater detail in FIGS. 2-5, include a front cover 2, a nightlight cover or lens 15, a plug deck assembly 10, and a main housing assembly 20. In the preferred embodiment, the housing assemblies are ultrasonically welded together, and the lamp cover or lens 15 is attached by a snap fit. It will be observed that the exterior of the thermal diffuser 1 is comprised of exterior portions of the front cover 2, the main housing assembly 20, the plug deck 10, and the nightlight lens 15.

In FIG. 1, the nightlight lens 15 is shown as the topmost element of the thermal diffuser 1. The nightlight lens 15 is preferably a molded plastic, such as clear polypropylene, polycarbonate, styrene, or nylon, so shaped as to fit tightly over the top portions of the main housing assembly 20 and plug deck assembly 10, when assembled as in FIGS. 1 and 3. While the nightlight lens may preferably be of a transparent plastic molding, it may also be translucent, colored, and/or decoratively adorned. The lens may also take any desired shape, and may be in a decorative form if so desired. In one preferred arrangement, the lens can be constructed with one or more shaped cutouts or windows, through which the light can pass, so as to project images on a wall or other surface. Further, while the figures illustrate the invention with the nightlight at the top, it is possible to orient the dispenser with the nightlight at the bottom or to the side, dependent upon the electrical outlet utilized.

FIG. 1 further illustrates the exterior frontal view of the front cover 2, which has air diffusion outlets 5 formed therein for diffusion of vaporized active material to the atmosphere. The diffusion outlets 5 each constitute a slot at the top of the front cover 2, and provide for a chimney effect so that air movement occurs across the front of an active material cartridge contained in a compartment or slot 6 formed in the housing 11. The diffusion outlets 5 may be formed in the front cover 2 during molding thereof. Air diffusion inlets 4 are illustrated in the front of the front cover 2, providing a source of airflow through the diffuser 1. Such inlets 4 are preferably decorative in nature as well, and formed in the front cover 2 during molding thereof.

Figure 3:
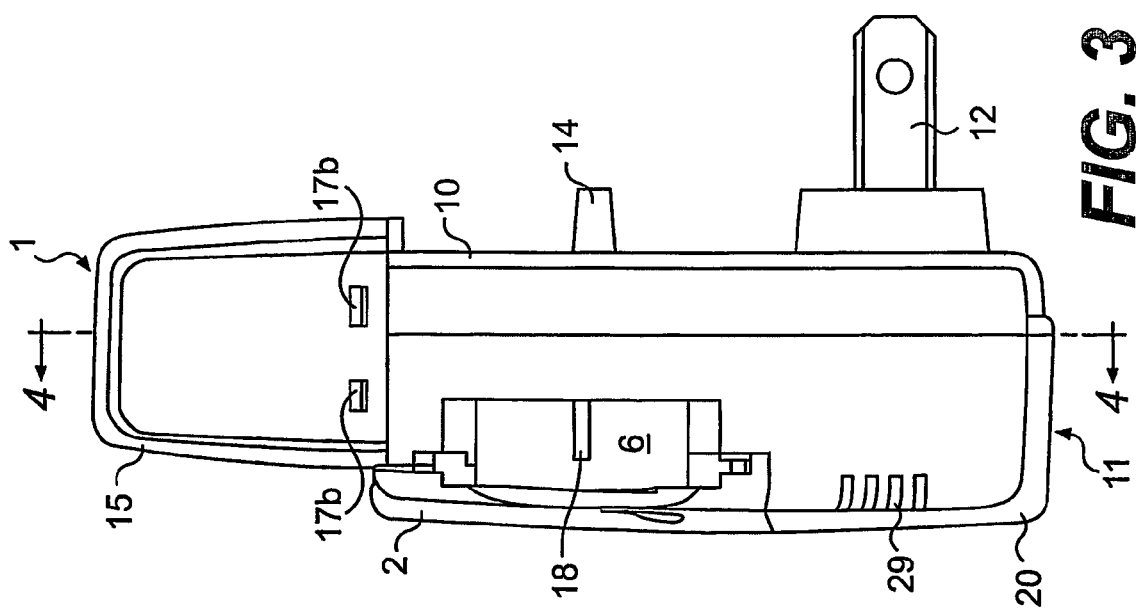
FIG. 3 is a side view of the plug-in diffuser of FIG. 1, showing the housing and external components of our invention.

The main housing assembly 20 has a slot 6 formed in its side, as best seen in FIGS. 2 and 3, to receive an active material cartridge or container (not shown). Within the slot 6, a rail 18 is formed, which engages protrusions or indentions on the cartridge during insertion, and holds the cartridge in position within the slot. Preferred containers for the present invention comprise tray-shaped cartridge containers having a plastic laminate over the active material, the laminate comprising an outer removable layer which is impermeable to the both liquid and vapor forms of said active material, and an inner layer which is impermeable to the liquid form, but permeable to the vapor form of the active material. Upon removal of the outer layer, the active material may diffuse through the remaining layer to be released to the atmosphere. Typical containers for holding the active material are those refill units sold under the trade name GLADE®, by S.C. Johnson & Son, Inc. Such cartridges are described in U.S. Pat. No. 4,849,606. While these preferred cartridges are described as being primarily used with air freshener active materials, the active material may be any material the diffusion rate of which can be enhanced by the application of heat. Such active materials include organic and synthetic air freshener compositions, insect control compositions (repellants and insecticides), sanitizers, and the like. Suitable examples of air freshener compositions are further described in the '440 patent. Suitable examples of insect control compositions usable with heated diffuser of the present invention are further described in U.S. Pat. Nos. 6,503,459 and 6,337,080, both of which are made by S.C. Johnson & Son, Inc. of Racine Wis. U.S. Pat. No. 6,482,863, also assigned to S.C. Johnson & Son, Inc. of Racine Wis., describes insect control compositions suitable for use with an alternative embodiment of our invention having a piezoelectric device. Alternatively, the diffuser may advantageously be designed as a container which itself holds a suitable active material to be heated, or a port could be provided to which separately provided containers might be attached. In particular, the instant diffuser could preferably employ a container of liquid active material, such as scented oil. A description of suitable scented oils and containers can be found in, for example, U.S. Pat. No. 5,647,053.

Also shown in FIG. 1, at the lower part of the diffuser, an electrical receptacle 3 is provided, into which an external plug may be inserted. The electrical elements behind this receptacle are shown more clearly in FIGS. 2, 4, and 5.

The nightlight of our invention is preferably of the "always on" variety. That is, the nightlight will be illuminated continuously whenever the diffuser 1 is plugged into a wall socket. Since the nightlight of our invention uses significantly less energy than a conventional nightlight, it is not necessary that the nightlight include an on/off switch. A preferred circuit for this "always on" type of nightlight is described in detail below with reference to FIG. 6. Alternatively, however, the nightlight of the present dispenser could be controlled by a conventional manual on/off switch 140, or by an automatic circuitry including an ambient light sensor device 22. Preferred circuits for use with a nightlight having these alternative arrangements are described below with reference to FIGS. 7 and 8, respectively. Also, more complex control of the operation of the light, including picking a specific color to be displayed, may be provided to a user, as described in more detail below.

If it is desired to provide the nightlight element of this invention with an ambient light sensor device 22 for automatic operation, the light sensor device 22 may preferably be located behind a sensor grill 29, in a position where it will not be significantly illuminated by the nightlight's light source, and will be protected from accidental breakage. The details of a nightlight having an ambient light sensor device are described in detail in the '440 patent.

FIG. 2 depicts a side cross section of the thermal diffuser 1 of FIG. 1, taken along line 2-2. FIG. 2 illustrates the nightlight lens 15, the front cover assembly 2, the main housing assembly 20, and the plug deck assembly 10. Also shown is the lighting element 7 electrically connected to a printed circuit board 21 and positioned under the nightlight lens 15. The heating element 8 is secured to the main housing assembly 20. Wall spacers 14 are provided on the rear (wall side) of the main housing assembly 20, which serve to stabilize the diffuser 1 when it is plugged into a wall outlet by plug 12.

FIG. 3 is a side view of the diffuser and clearly shows the opening 6 for receipt of the active material cartridge from the open or receiving end. The nightlight lens 15 is attached to the plug deck 10 and the main housing assembly 20 by retention clips 17b that extend to engage holes formed in the nightlight lens 15.

FIG. 4 illustrates a cross-sectional view of the diffuser of FIG. 3, taken on line 4-4, and provides a view of the interior of the diffuser 1, looking from the rear (wall side) toward the front thereof. This figure shows the interior surface of the nightlight lens 15, and the back of main housing assembly 20. Mounted to the back of the main housing assembly 20 is the heating element 8, held in place by a pair of clips 24. Terminals 9 are made of an electrically conductive material, such as copper, and make electrical contact with the male plug 12 (not visible in this figure) to transfer power to the heating element 8. In addition, the terminals 9 serve as heat transfer elements to enhance the transfer of heat from the heating element 8 to the active material. Since the wall of the main housing assembly 20 forms the back wall of the slot 6, which receives the active material cartridge, the terminals 9 act to transfer heat to the active material, thereby increasing the rate of diffusion thereof. Also in electrical contact with the terminals 9 is the nightlight printed circuit board 21, which is made of a suitable circuit board material, and which provides mounting means and circuitry to provide electricity to the nightlight, and the optional illumination sensor and its circuitry. The circuitry of the nightlight printed circuit board 21 is described in detail below. Also shown in FIG. 4 are retention clips 17a, for positioning and retaining the terminals 9 on the main housing assembly assembly 20. The internal electrical structure (female assembly) of the receptacle 3 is also shown at 13.

Figure 5:
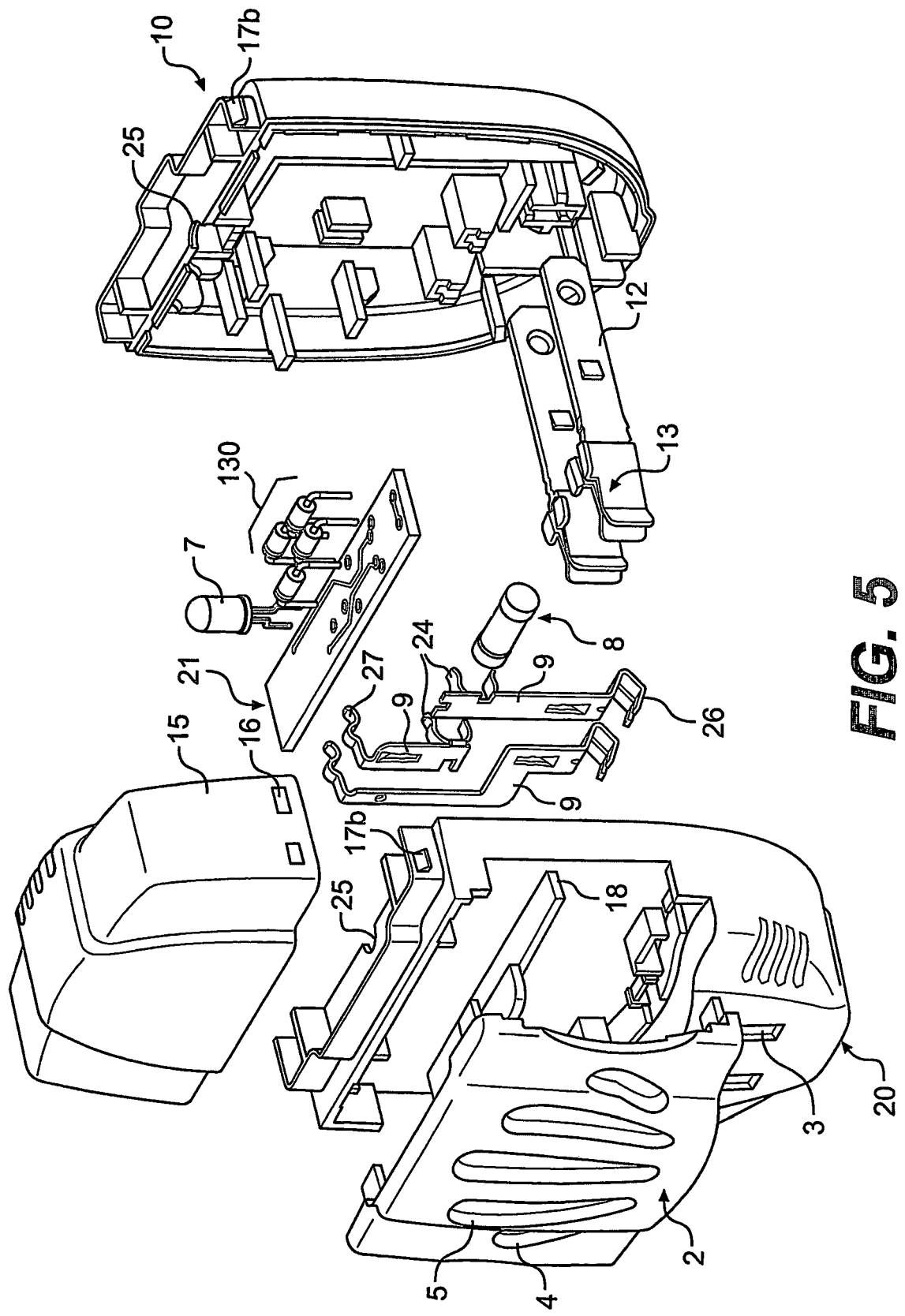
FIG. 5 is an exploded view of the plug-in diffuser of FIG. 1, showing the internal electronic components of the diffuser.

In FIG. 5, the diffuser 1 is shown in an exploded view. The plug deck assembly 10 is illustrated, with the plug unit 12 of the diffuser 1 shown in a "withdrawn" position, prior to being inserted through plug holes formed in the plug deck assembly 10. At the internal end of each of the prongs of the plug 12 is a female assembly or receptacle 13 for acceptance of an external plug through the external receptacle 3 in the main housing assembly 20. In this manner, the diffuser 1 of the present invention provides a plug-through outlet that allows the user use to an additional electrical appliance without need for another wall socket.

The slot 6 and positioning rail 18, for accommodating and retaining the cartridge of active material, are also visible in FIG. 5. In conjunction with the front cover assembly 2, the main housing assembly 20 forms the slot 6 into which the active material cartridge may be placed. This cartridge, when in position, will be in close proximity to the front surface of the main housing assembly 20, such that heat generated by the heating element 8 at the back face of the main housing assembly 20 will be transferred to the front face of the main housing assembly 20, where it will act to evaporate active material in the cartridge. The terminals 9 are attached to the back face of the main housing assembly 20. As mentioned above, these terminals 9 are preferably made of a material such as copper, brass, bronze, or the like, which is both electrically and heat conductive. These terminals have spring contacts 26, by which electrical contact is made with the internal portions of the prongs of plug 12, when the plug 12 is inserted into an electrical outlet. Electricity is transmitted from the outlet, via plug 12, to spring contacts 26 of the terminals 9. The terminals 9, being electrically conductive, conduct electricity to the heating element 8 via clips 24, thereby activating the heating element 8. Heat generated by the heating element 8 is transferred to the inner surface of the main housing assembly 20, and by conduction to the terminals 9. The terminals 9, being in direct contact the main housing assembly 20, greatly increase the efficiency of the heat transfer to the active material cartridge. Simultaneously, the terminals conduct electricity to the nightlight printed circuit board 21, via spring contact elements 27, at the end of the plates. The contact elements are configured so as to contact electrically conductive circuits on the surface of the nightlight printed circuit board 21, thus providing power to the lighting element 7. The nightlight printed circuit board 21 has a bridge circuit 13 comprising four diodes D1-D4 disposed thereon. The diodes are connected to one another by circuitry on the printed circuit board 21 in the configuration shown in FIGS. 6-8. Also illustrated in this figure is a notch or opening 25 in the surface of the main housing assembly 20 and the plug deck assembly 10 to support, and aid in positioning of, the lighting element 7. While the foregoing description is of a preferred construction of the electrical system, it should be understood that our invention could be suitably carried out wholly or in part using other types of conductors, such as wires, printed circuit boards, and the like, and other types of electrical connections, such as crimping, soldering, welding, or the like.

The nightlight lens 15 is configured to be held in place by retention clips 17b provided on the plug deck 10 and the main housing assembly 20 for engagement with correspondingly located clip receptacles 16 in the nightlight lens 15.

The heating element 8 is held in place on the main housing assembly 20 by heating element clips 24, which, as previously discussed, are in electrical and heat conductive contact with terminals 9.

The electronic circuitry of our invention is described below with reference to FIGS. 6-8. In these figures, V represents an input voltage from an alternating current wall socket. A brief description of each of these circuits is provided below. However, the drawing figures alone should be sufficient for one of ordinary skill in the art to make and use our invention.

Figure 6:
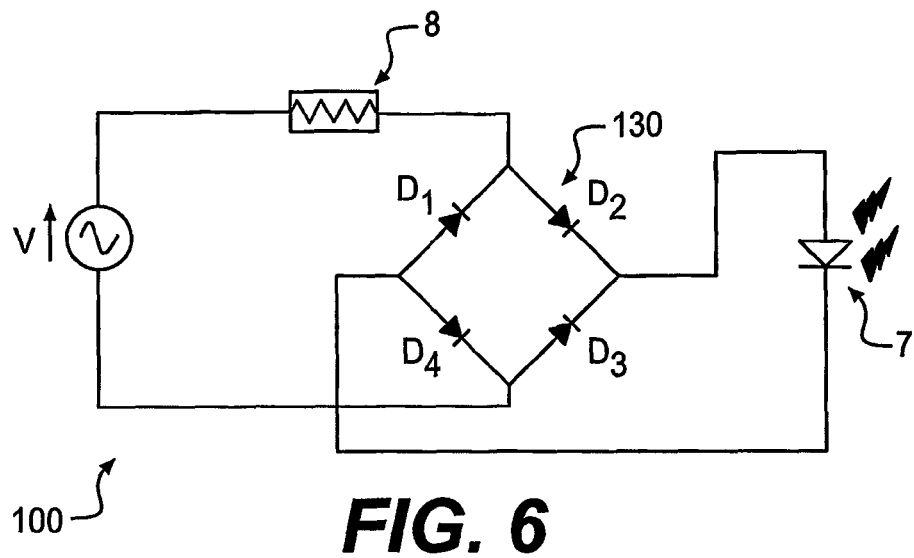
FIG. 6 is a circuit diagram of a preferred circuit usable with our invention.

FIG. 6 shows a circuit diagram of a preferred circuit used with our invention. The circuit 100 of FIG. 6 comprises a resistance heating element 8, a bridge circuit 130, and an LED lighting element 7. Briefly, diodes are electronic devices that offer unequal resistance to forward and reverse current flows. Current is allowed to easily flow through the diodes from the anode to the cathode (in the direction of the triangle), but current flow in the opposite direction is restricted. The bridge circuit 130 is of a conventional type, the use of which is well known in the art. The bridge circuit 130 is comprised of four diodes D1-D4 arranged to allow current to flow through the LED lighting element 7 in the same direction regardless of the change in polarity of the alternating current from the wall socket. When the current from the wall socket is flowing in the direction indicated by the arrow in FIG. 6, the current travels through the heating element 8, through diode D2, through the LED lighting element 7, and then through diode D4 to complete the circuit. When the current from the wall socket travels in the direction opposite the arrow in FIG. 6 (i.e., when the alternating current has the opposite polarity), the current is allowed to travel through diode D3, through the LED lighting element 7, though diode D1, and through the heating element 8 to complete the circuit. This is known as a full wave rectification circuit because both the positive and negative portions of the alternating current wave form (the full wave) are normalized and provided to the LED lighting element 7.

Alternatively, instead of a full wave rectification circuit, a half wave rectification circuit could also be used. However, the half wave rectification circuit is less desirable because it will only supply power to the LED lighting element during one polarity of the alternating current wave form, thus, the LED lighting element will only be on approximately 50% of the time. The other half of the time, the LED will be off. Accordingly, using a half wave circuit will produce a flickering appearance of the LED lighting element.

Figure 7:
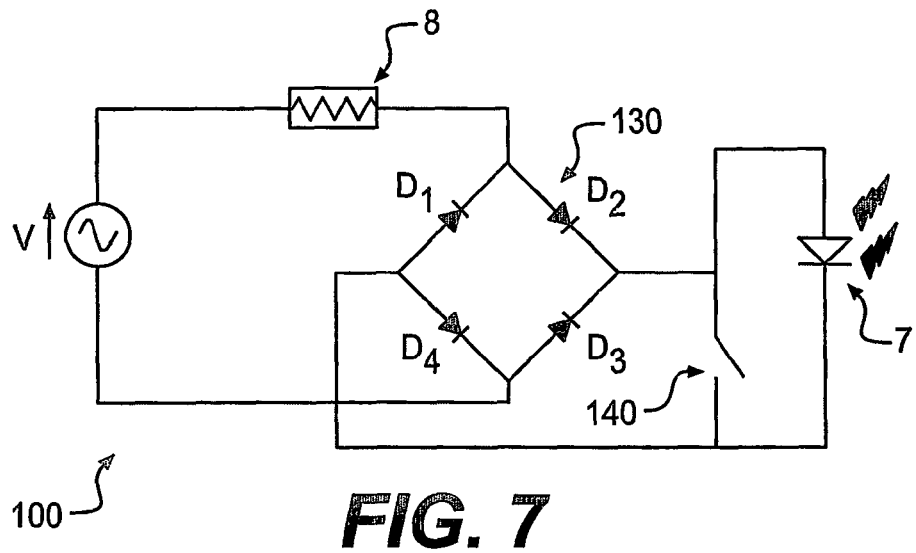
FIG. 7 is a circuit diagram of another preferred circuit usable with our invention, and having a switch.

FIG. 7 depicts a circuit diagram of another preferred circuit of our invention. The circuit shown in FIG. 7 is similar to the one shown in FIG. 6, except that a switch 140 is provided to turn the LED lighting element 7 on and off. The switch 140 is preferably a manual on/off switch, although any type of switch, manual or automatic, may advantageously be used. The circuit diagram of FIG. 7 shows the switch 140 in an open condition, such that the LED lighting element 7 is turned on. When the switch 140 is open, the circuit functions in the same manner as the circuit of FIG. 6. When, however, the switch 140 is closed, the circuit will bypass the LED lighting element 7, such that the heating element 8 is activated, but the LED lighting element 7 is not. With the switch in this closed position, current traveling in the direction of the arrow in FIG. 7 will travel through the heating element 8, through diode D2, through the switch 140 (which is now closed), and through diode D4 to complete the circuit. When the current from the wall socket travels in the direction opposite the arrow in FIG. 7 (i.e., when the alternating current has the opposite polarity), the current is allowed to travel through diode D3, through the switch 140 (which is now closed), though diode D1, and through the heating element 8 to complete the circuit.

Figure 8:
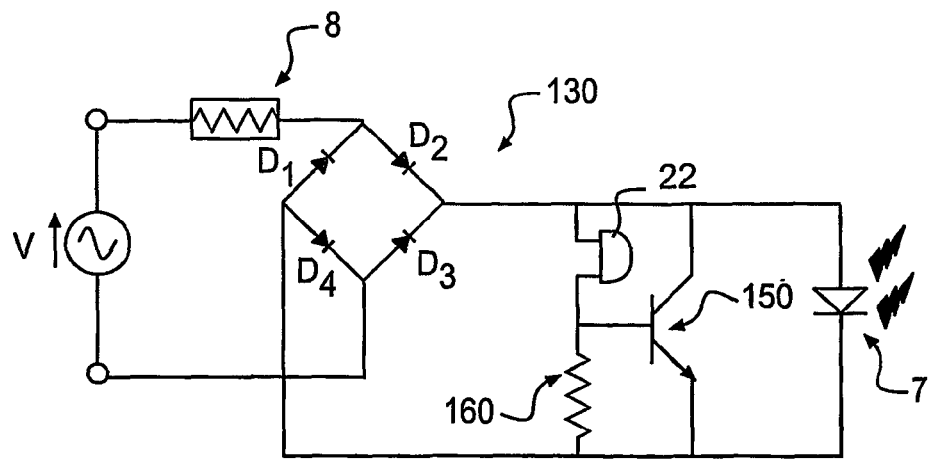
FIG. 8 is a circuit diagram of yet another preferred circuit usable with our invention, and having a light sensor device 22.

FIG. 8 depicts a circuit diagram of yet another preferred circuit of our invention. In this circuit an ambient light sensor device 22 is used to automatically actuate the LED lighting element 7 when the light sensor device 22 detects that the surrounding room is dark. The application of an ambient light sensor to a diffuser having a nightlight is discussed in detail in the '440 patent. The circuit depicted in FIG. 8, is similar to that of FIG. 6, except that it also includes a transistor device 150, a second resistor device 160, and a light sensor 22. In this circuit, when the light sensor 22 detects light it causes the transistor 150 to conduct, such that current will bypass the LED lighting element 7 (i.e., when current travels in the direction shown by the arrow in FIG. 8, current travels through the heating element 8, through diode D2, through transistor 150, and through diode D4 to complete the circuit). However, when the light sensor 22 detects that the room is dark, the transistor 150 will open, thereby forcing current to flow through the LED lighting device 7 following the same path as in the circuit of FIG. 6. Substantial current will not flow through the light sensor 22, because the second resistor 160 has a much higher resistance than does the LED lighting device 7.

A current limiting capacitor could be used with any of the foregoing circuits to further smooth the current flow in a known manner. As illustrated in FIGS. 6-8, however, a current-limiting capacitor is not required to successfully practice our invention, since the bridge circuit greatly smoothes the current. Of course, such a current limiting capacitor could be used if desired for particular applications where current fluctuation due to the alternating current is to be minimized, such as where extremely constant light intensity is important. Since no current-limiting capacitor is required, the cost of producing our invention is further reduced, as compared to other existing nightlight devices.

As may be readily observed from the figures, the operation of the thermal diffuser 1 of our invention is relatively straightforward. The operation of one preferred embodiment of our invention having a circuit like that of FIG. 6 is described below.

After insertion of an active material cartridge into slot 6, the diffuser unit 1 is plugged into an electrical receptacle of a wall outlet, using diffuser plug 12. The heating element 8 is powered via electricity passing through the plug 12, the protrusions 26 of the terminals 9, the terminals 9, and the heating element clips 24. Thus activated, the heating element 8 generates heat, which is transferred by radiation and by conduction through terminals 9, to the back surface of the wall of the main housing assembly 20. The active material cartridge, being in close proximity to the opposite side of the main housing assembly 20, absorbs heat energy, causing the active material to be heated and evaporated, thereby diffusing the active material into the air and passing into the atmosphere through diffusion outlets 5. The air freshener dispenser is stabilized in the wall outlet by the presence of the wall spacers 14 on the rear of the unit. In addition, the lighting element 7 automatically lights when the diffuser 1 is plugged into a wall socket (in the case of an "always on" diffuser). That is, the lighting element 7 is in an "always on" condition. In addition, an additional electronic appliance can be plugged into the receptacle 3 on the front of the diffuser 1.

Diffuser with Shine-Through

Figure 9:
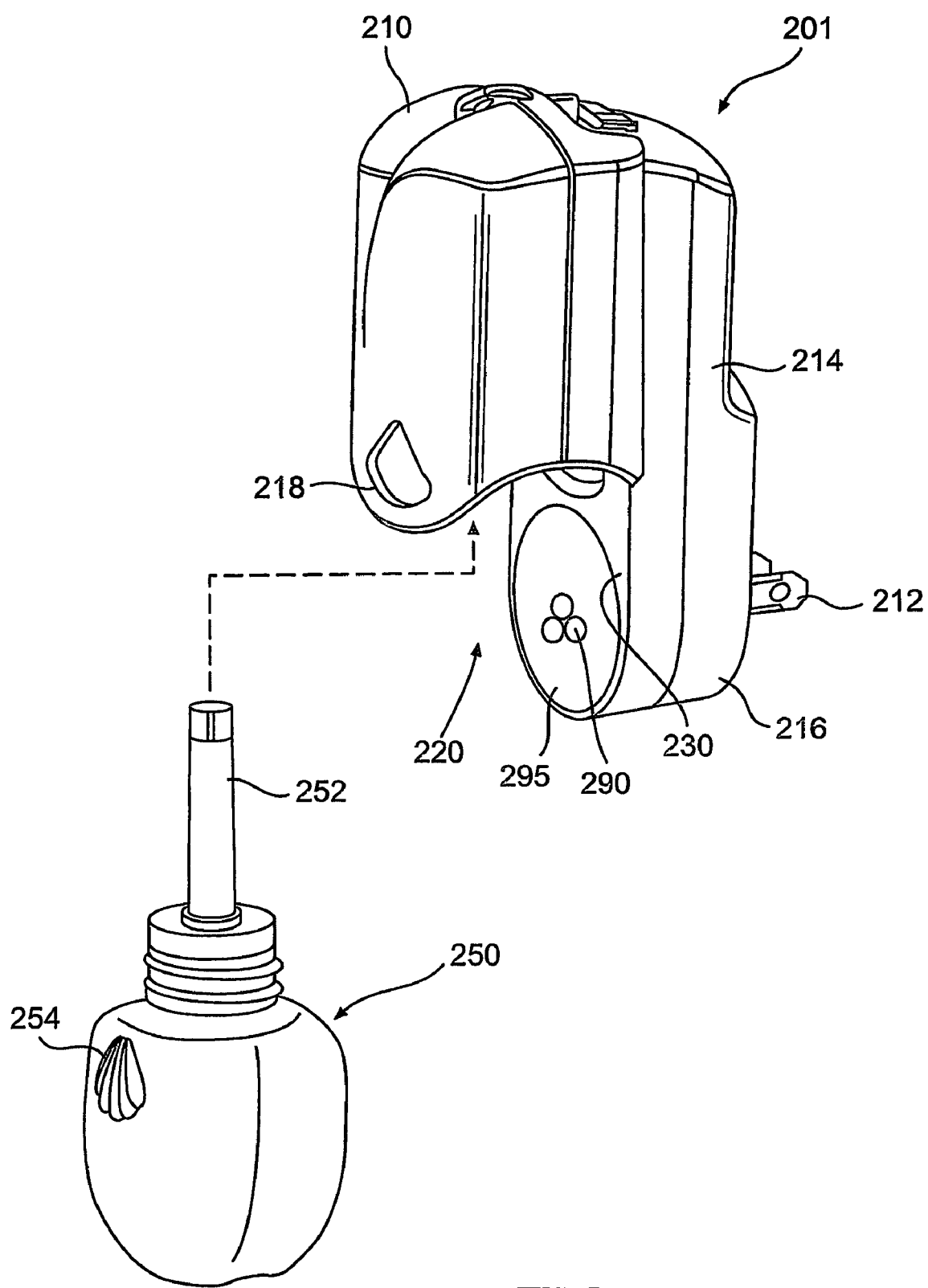
FIG. 9 is a perspective view of another preferred embodiment of our invention, wherein light from a lighting element shines through a container of active material.
Figure 10:
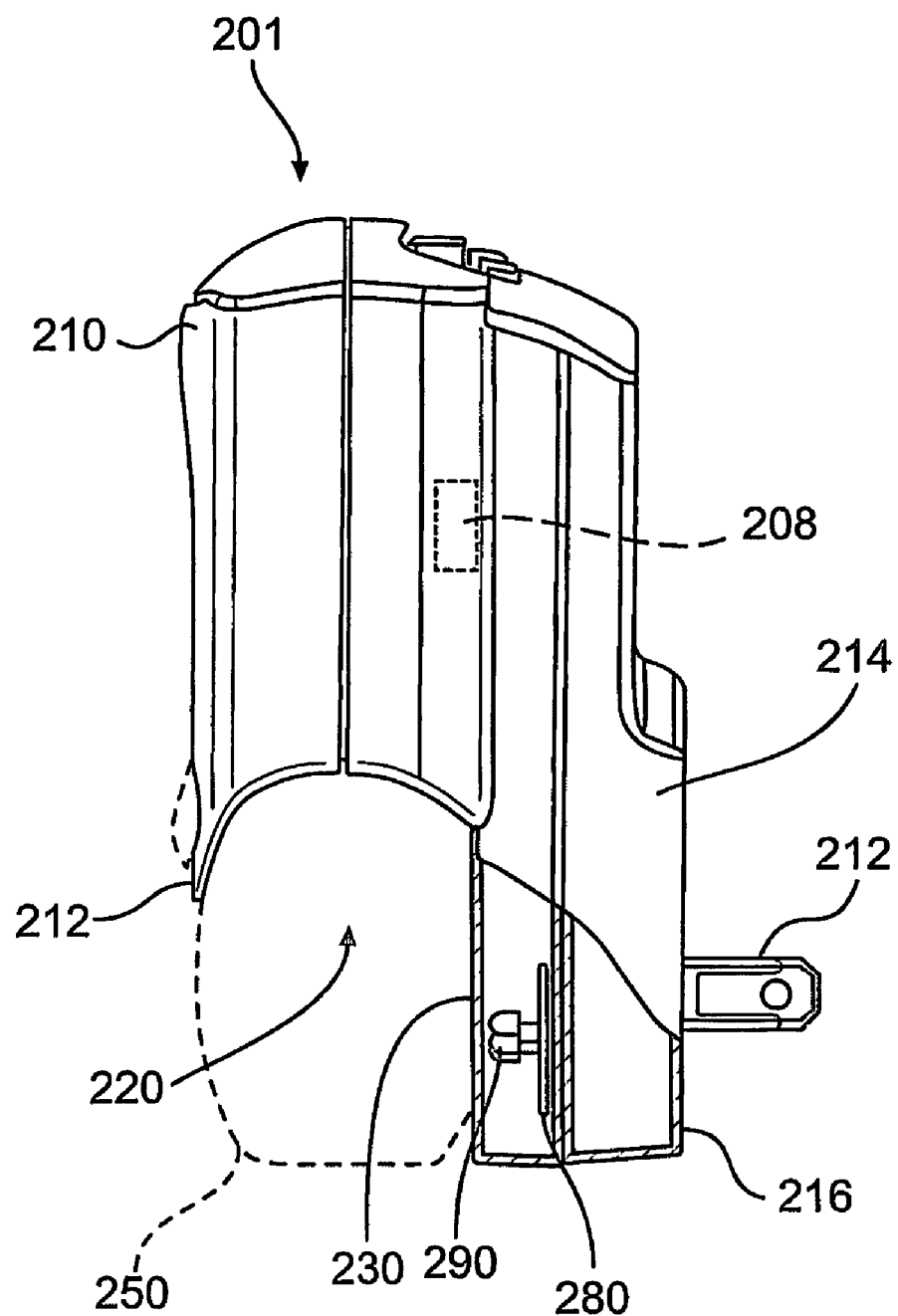
FIG. 10 is a side view of the device of FIG. 9.

In another aspect, a diffuser according to our invention may include a shine-through feature wherein light from a lighting element shines through a container of active material. A preferred embodiment of the shine-through feature is illustrated in FIGS. 9 and 10. The shine-through feature is broadly applicable to any type of diffuser having a translucent or transparent holder of active material, including diffusers using active material gel cartridges, such as those described in U.S. Pat. No. 4,849,606, and those using containers of liquid active agent, such as those described in U.S. Pat. No. 5,382,410. The general premise of this embodiment is that the lighting element is located behind the active material container, so that the emitted light shines through the active material.

In the preferred embodiment shown in FIGS. 9 and 10, the active material is a liquid active material, such as a scented oil air freshener material, an insect control agent, or the like, and the lighting element preferably comprises at least one LED. More preferably, the at least one LED comprises plural LEDs or LED arrays, which may be controlled together or independently.

As illustrated in FIG. 9, a diffuser 201 according to this embodiment generally comprises a housing 210 having a compartment 220 configured to receive and releasably hold a container 250 of liquid active material, an electrical plug 212 for connection of the diffuser 201 to a power source, and at least one LED 290 positioned at a back surface 230 of the compartment 220, such that when the active material container 250 is received in the compartment the at least one LED 290 shines through the active material. The diffuser 201 preferably also comprises a heating element 208 to enhance the diffusion of the active material.

The construction of the housing 210 in this embodiment is not critical. The shine-through feature could advantageously be incorporated into the housing of virtually any diffuser. Preferably, however, the housing 210 is made of a thermoplastic material and is injection molded. In the particular embodiment shown in FIGS. 9 and 10, the housing 210 includes an upper portion 214 and a lower portion 216, which are fastened together by heat-staking or any other suitable fastening means, including, for example, rivets, press fit, snap fit, screws, ultrasonic welding, adhesives, or the like.

In this embodiment, the upper portion 214 of the housing 210 substantially forms the compartment 220 into which the container 250 is inserted. The front surface of the upper portion 214 of the housing has an opening 218 for engaging a raised pattern 254 of the container 250 to releasably hold the container 250 in place in the housing 210 during use. The front surface of the upper portion 214 of the housing 210 is sufficiently pliant so that pulling the container 250 in a downward direction causes the raised pattern 254 to release from the opening 218 in the front the front surface of the upper portion 214 of the housing 210, thereby enabling removal of the container 250 from the diffuser 201. Alternatively, a neck portion of the bottle may be designed to snap to, or screw into, the housing 210. Suitable refill bottles are available in a wide variety of liquid formulations from S.C. Johnson & Son, Inc., of Racine, Wis., under the GLADE® PLUGINS® SCENTED OIL® and RAID® brand names.

The at least one LED 290 is preferably recessed in the back surface 230 of the housing 210 to accommodate the container 250 in the compartment, and is electrically connected to the plug 212, preferably via a printed circuit board 280, as shown in the cut-away portion of FIG. 10. Preferably, the at least one LED 290 comprises a plurality of LEDs of different colors. When a plurality of LEDs 290 are used, they can be arranged in any shape or configuration, and may be movable within the housing 210. For example, LEDs 290 could be mounted in a circle in a rotatable platform 295, which rotates relative to the housing 210, so as to provide a changeable light display.

Preferably, the heating element 208 is a metal oxide resistor potted in a ceramic block, which is capable of handling up to at least about 5 W. One suitable resistor is a 6 kΩ resistor, capable of handling 5 W. Alternatively, the heating device 250 can comprise any other suitable type of heating device, such as a resistance heater, a wire-wound heater, a PTC heater, or the like.

The plug 212 may be disposed in either the upper or lower portion 214, 216, of the housing 210, or may be configured as a separate element that is interposed between the upper or lower portions 214, 216 of the housing during assembly. Preferably, the plug 212 is secured to the multi-piece housing 210 in a manner that allows the plug 212 to rotate relative to the housing 210, in order to support the diffuser 201 in an upright position in both horizontal and vertical wall outlets. However, the plug 212 need not be rotatable, particularly if the diffuser is configured with a remote-use assembly as described in more detail in the description of the remote-use embodiments below.

As in the first embodiment, the diffuser of this embodiment is preferably of the "always on" variety, such that the LED(s) 290 will be illuminated continuously whenever the diffuser 201 is plugged into a wall socket. The circuit shown in FIG. 6 is illustrative of this embodiment as well. Alternatively, LED (s) could be controlled by a conventional manual on/off switch (of which FIG. 7 is illustrative), or by an automatic circuitry including an ambient light sensor (of which FIG. 8 is illustrative).

Optionally, the printed circuit board 280 may also include one or more controllers, memories, and/or processors for controlling operation of the at least one LED 290 and the heating element 208. Preferably a light controller could be provided to control the color and/or intensity of the LED(s) 290, and a fragrance controller could be provided to control the rate of diffusion of the active material by varying the heat emitted from the heating element 208. Further, both controllers may be provided and operated in a coordinated manner, so as to produce a predetermined presentation. In particular, a programmable processor may be used to allow a user to program the operation of the fragrance controller and light controller to control at least one of (i) the rate at which the active material is diffused over the course of the presentation, and (ii) at least one of the color and intensity of at least one of the plurality of light emitting diodes, to produce a desired presentation over a set period. Suitable control options are described in more detail in the section entitled Diffuser with Coordinated Emission of, Light, and/or Sound.

The shine-through feature of this embodiment could easily be adapted for use in any of the other embodiments disclosed herein. For example, the diffuser with LED nightlight of FIG. 1 could be easily modified to include the shine-through feature of this embodiment by simply moving the nightlight LED 7 of that embodiment to a location on the back surface of the compartment 6, so that it will be behind and shine through the active material cartridge when it is inserted in the diffuser. Alternatively, shine-through LED(S) could be added to the diffuser of the first embodiment in addition to the nightlight LED 7.

Diffuser with Remote-use Assembly

Plug-in diffusers generally plug directly into a wall socket, and are supported thereby. This arrangement is suitable for simple diffusers that only emit fragrance, since the exact location of the diffusers is not important. However, if a diffuser with a nightlight is plugged into a wall socket that is close to the floor or near a corner, the light from the nightlight will not effectively illuminate the area. Moreover, for a diffuser having an aesthetic display, such as the shine-through diffuser of the previous embodiment, it may be desirable to locate the diffuser in a location where it can be easily viewed. Thus, for diffusers having lighting elements, such as nightlights, shine-through features, or any of the other lighting features described herein, it may be preferable to locate the diffuser in a location that is remote from a wall socket.

Figure 11:
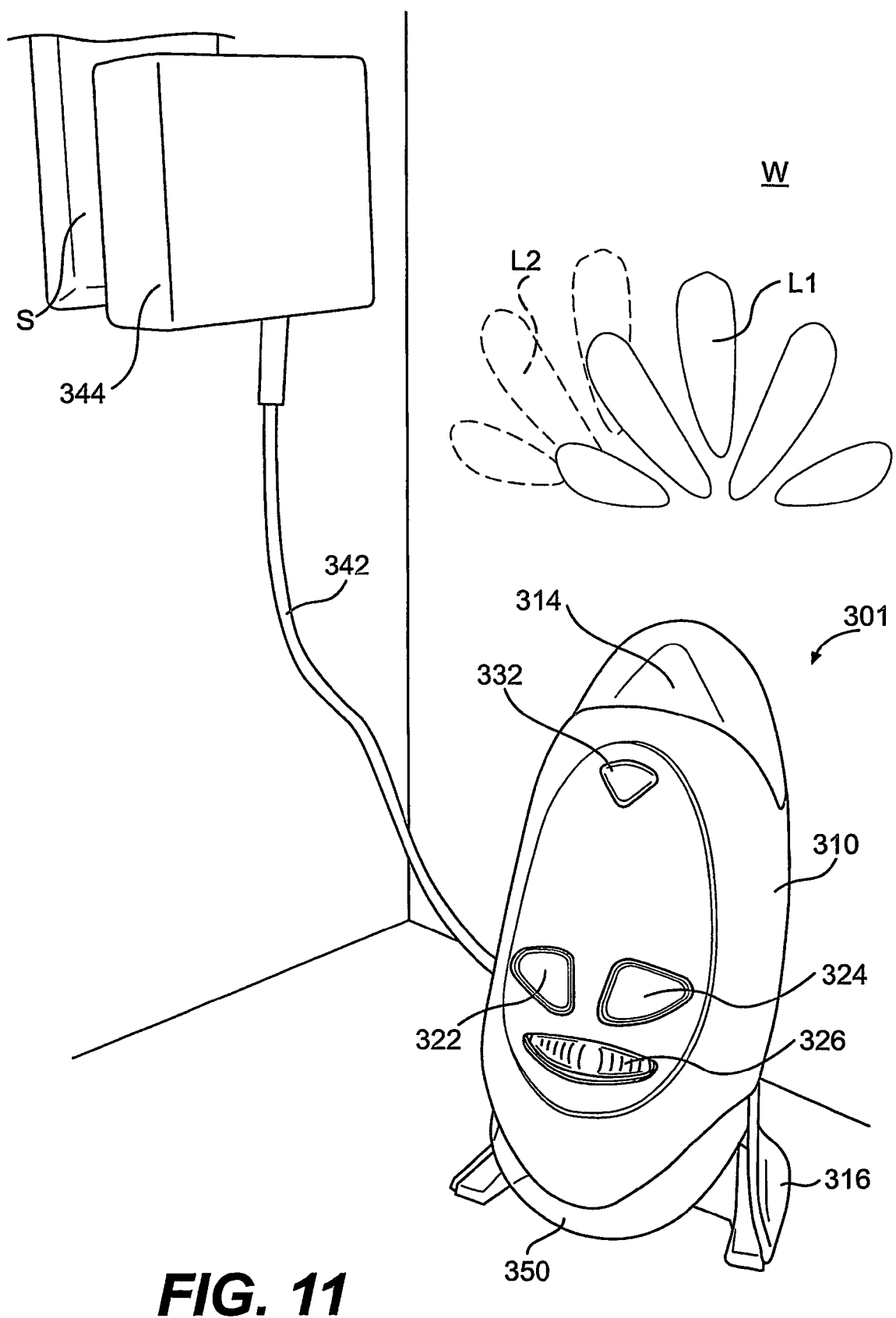
FIG. 11 is a perspective view of a diffuser according to another embodiment of our invention.
Figure 12:
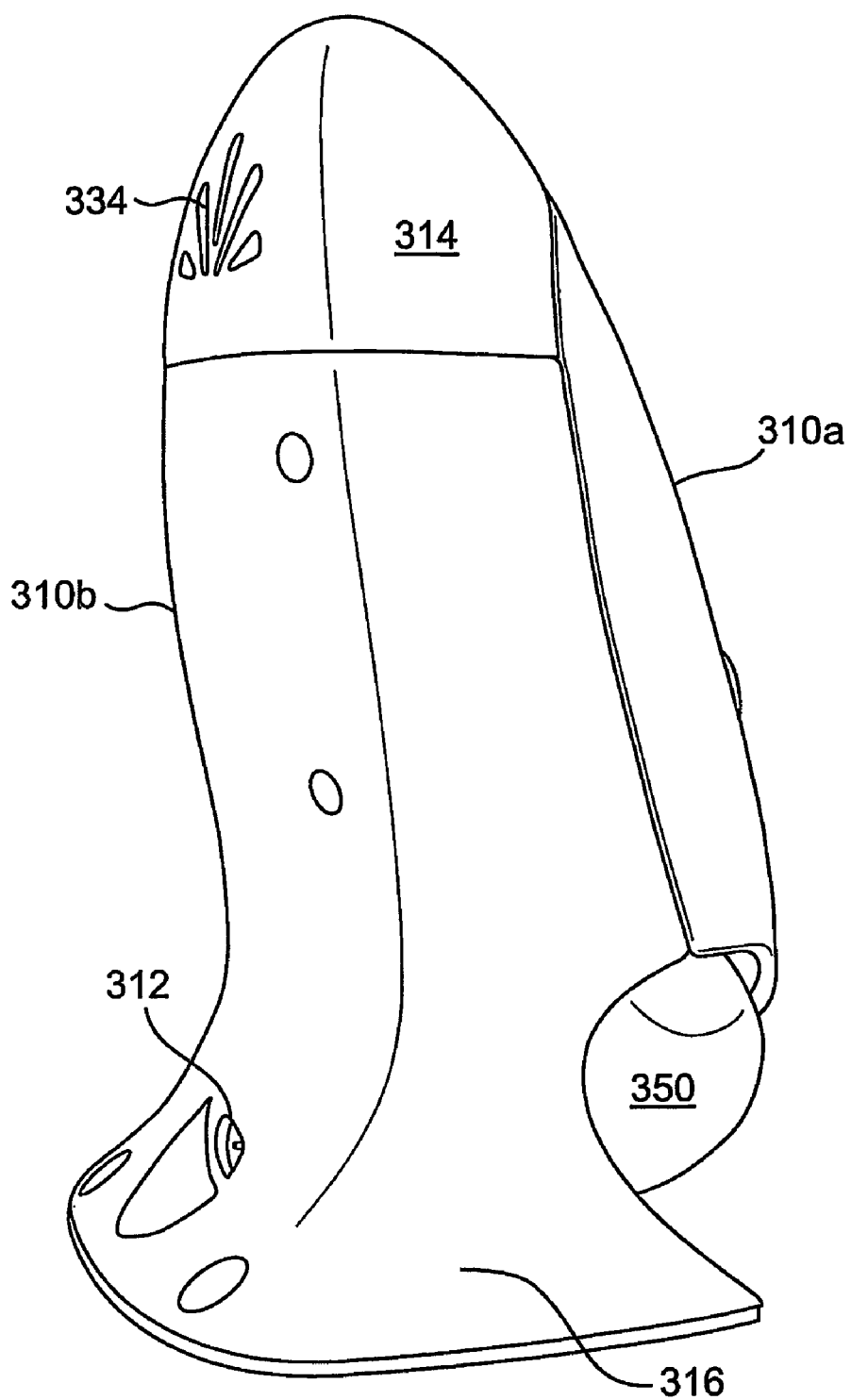
FIG. 12 is a rear perspective view of the diffuser of FIG. 11.
Figure 13:
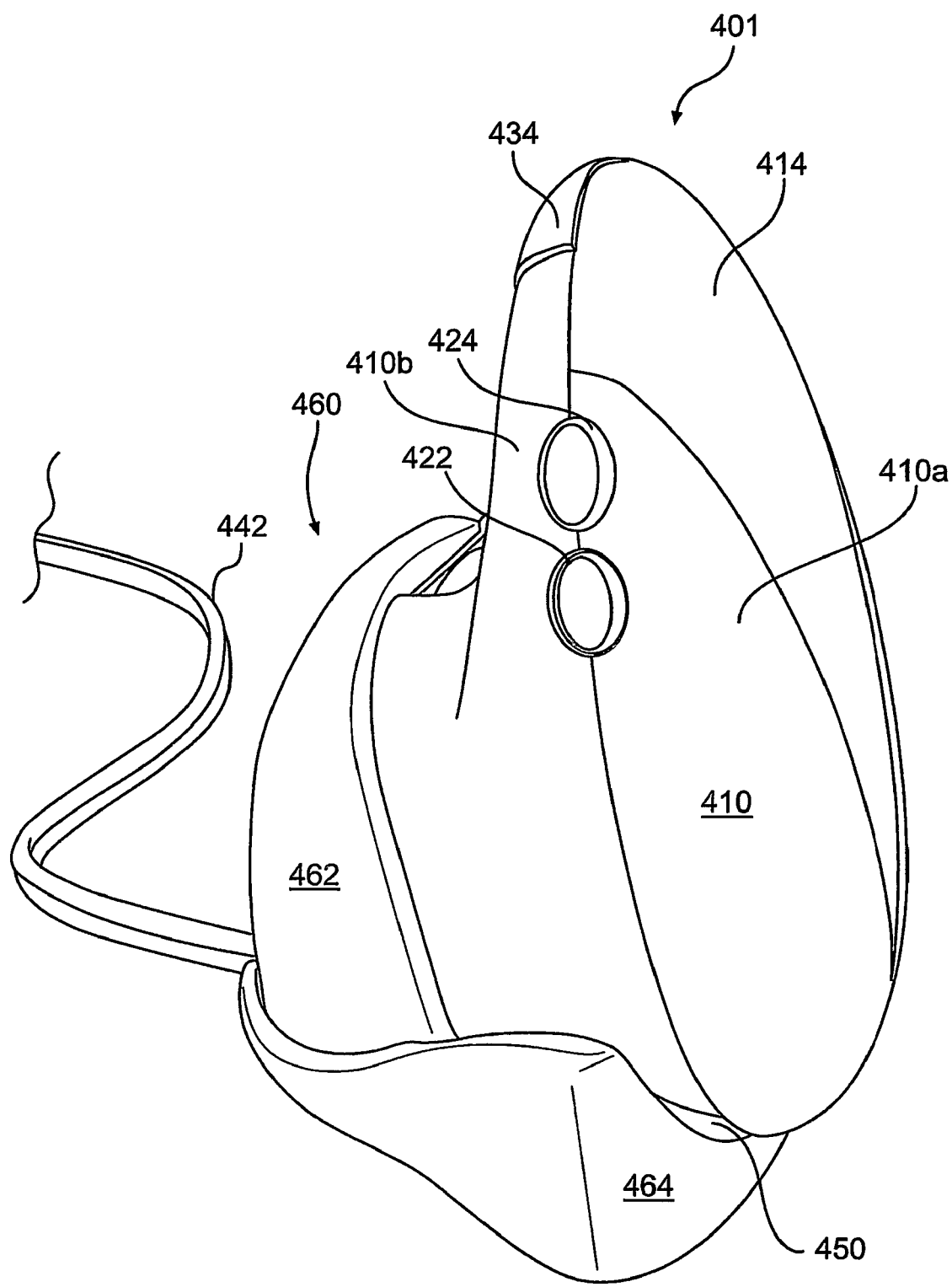
FIG. 13 is a perspective view of a diffuser according to another embodiment of our invention.
Figure 14:
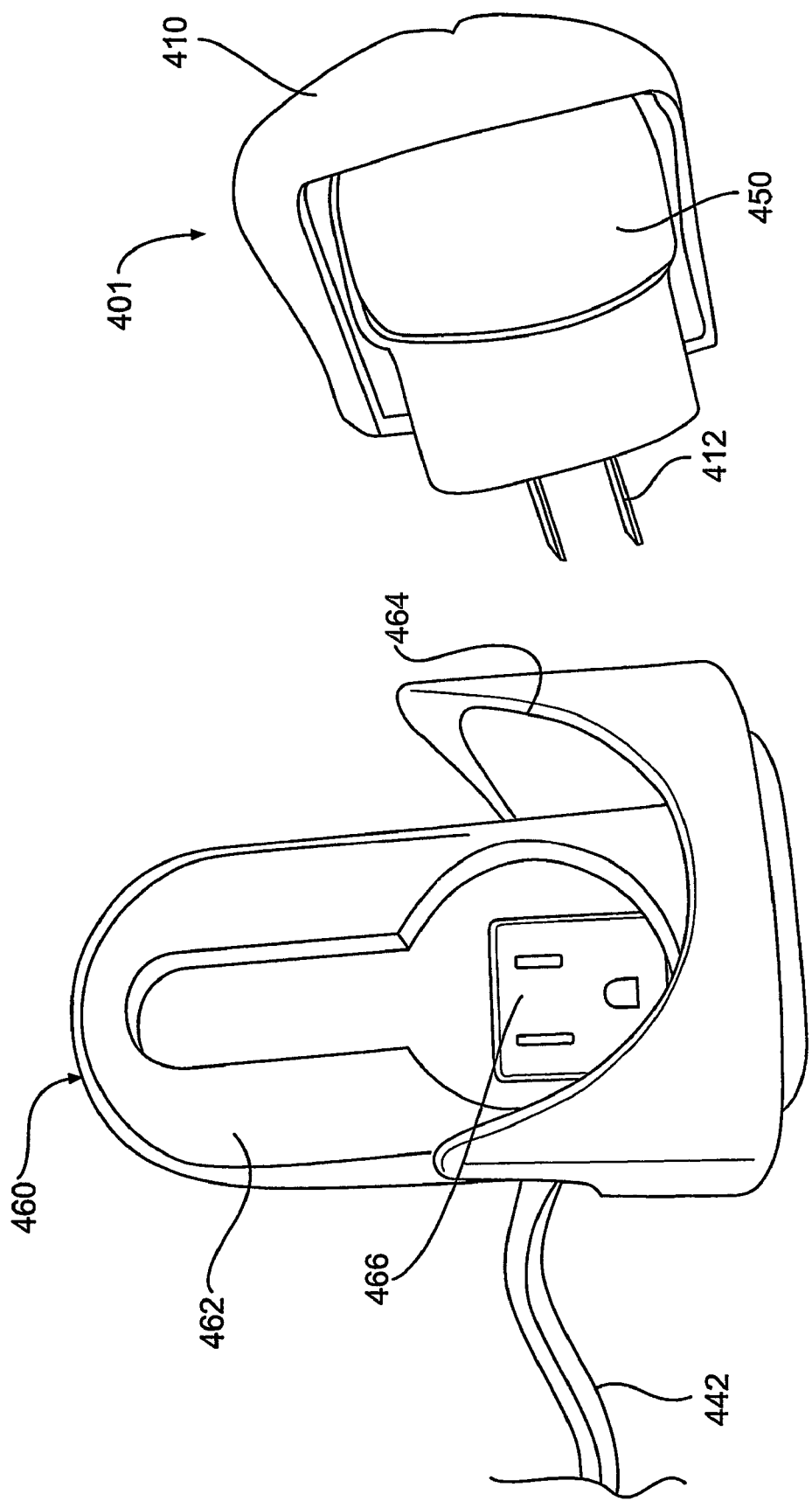
FIG. 14 is an exploded view of the diffuser of FIG. 13, showing the diffuser rotated approximately ninety degrees relative to the docking station to illustrate the bottom of the diffuser.

Accordingly, a diffuser according to another aspect of our invention, illustrated in FIGS. 11-14, includes a remote-use assembly that supplies power to the diffuser from a remote wall socket. Generally, the remote-use assembly comprises a support member that supports the diffuser on a support surface remote from a wall socket, and a cord that supplies power to a plug of the diffuser from the wall socket. Such a remote-use assembly may include either a direct-corded arrangement (i.e., a cord is connected directly to the diffuser, as shown in FIGS. 11 and 12), or a docking station arrangement (i.e., the diffuser is adapted for connection to a docking station, which is in turn connected to a remote wall socket, as shown in FIGS. 13 and 14). Of course, there is no requirement that the diffuser of our invention be separable from the remote-use assembly. Accordingly, a diffuser according to our invention may also preferably be provided with a cord fixedly attached to the diffuser to supply energy to the diffuser from a remote wall socket. In such a variation, the cord is not removable from the diffuser. Accordingly, the diffuser is preferably provided with a base coupled with the housing of the diffuser to support the diffuser on the support surface remote from the wall socket.

With any of these arrangements (direct-corded, docking station, or fixed-cord), the remote-use assembly may transmit alternating current (AC) from a wall socket directly to the diffuser, or the remote-use assembly may include a transformer/rectifier to step the supplied voltage from the wall socket and change the AC to direct current (DC), which is then supplied to the diffuser. Of course, any of the embodiments disclosed herein could employ a transformer/rectifier, or not, depending on the particular application and consumer preference.

Figure 12A:
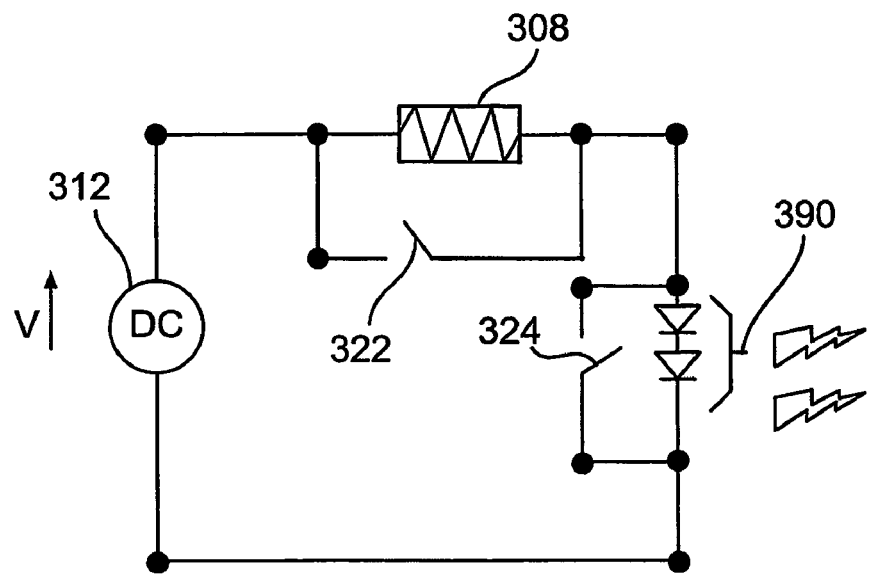
FIG. 12A is a circuit diagram of one configuration of the diffuser of FIG. 11.
Figure 12B:
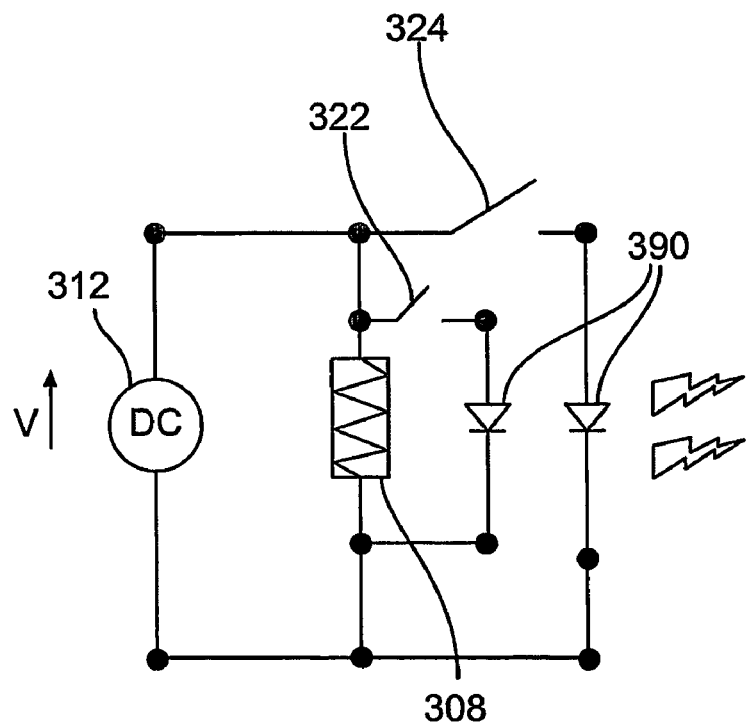
FIG. 12B is a circuit diagram of another configuration of the diffuser of FIG. 11.

The docking station is shown in FIGS. 13 and 14 without a transformer/rectifier, whereby high voltage AC is supplied directly from the wall socket to the diffuser, while the direct-corded arrangement is shown in FIGS. 11 and 12 with a transformer/rectifier, which steps down the voltage and rectifies the current supplied to the diffuser. Hence, the circuit diagram of the docking station embodiment shown will be substantially the same as that shown in FIG. 6 for a diffuser of the always on variety, FIG. 7 for a diffuser with a manual switch variety, and FIG. 8 for a diffuser with an ambient light sensor. The circuit diagram corresponding to the direct-corded embodiment shown will generally include a DC power source with a heating element and LED(s) connected either in series or in parallel with the heating element. Exemplary circuits corresponding to each of these direct-corded variations are shown in FIGS. 12A and 12B, respectively.

As shown in FIGS. 11, 12, 12A, and 12B, a direct-corded diffuser 301 according to this embodiment comprises a multi-piece housing 310 (having a front portion 310a and a back portion 310b), a container 350 of active material, and a heating element 308 (shown schematically in FIGS. 12A and 12B) similar to those described above with respect to the shine-through embodiment. Accordingly, details of the construction of those elements are omitted.

In addition, the diffuser 301 of this embodiment includes a remote-use assembly that supplies electrical energy to the diffuser 301 from a remote wall socket S. The remote-use assembly of this embodiment comprises a transformer/rectifier 344, a cord 342, and a receptacle (not shown) electrically connected to the cord. The transformer/rectifier 344 includes a wall plug (also not shown), which plugs directly into the wall socket S. The transformer/rectifier 344 steps down the voltage and rectifies the current (i.e., converts approximately 110 volts AC from the wall socket S to about 2-15 volts DC, depending on the desired characteristics and features of the diffuser) from the wall socket S. This stepped-down DC power is then supplied through the cord 342 to the receptacle, which attaches to a jack or plug 312 on the back portion 310b of the housing 310. This arrangement, using the transformer/rectifier 344, may be preferred from the safety standpoint, since the voltage supplied to the diffuser 310 is much lower than that at the wall socket S.

In the diffuser 301 of the direct-corded embodiment, the support member includes a base 316 coupled to the housing 310 to support the diffuser 301 on a support surface at a location remote from the wall socket S. As shown in FIG. 12, the base 316 is formed integrally with a back portion 310b of the housing 310. However, the configuration of the base 316 is not important. As long as the base provides a support to hold the diffuser in a desired orientation, it can effectively be formed integrally with any portion of the housing or could be provided as a separate element that is coupled to the housing 310 to hold the diffuser 301.

The diffuser 301 also includes an adjustment mechanism for varying the rate at which the active material is diffused. The adjustment mechanism adjusts the diffusion rate by moving a wick (not shown) of the container 350 towards (to increase the diffusion rate) or away from (to decrease the diffusion rate) the heating element 308, in accordance with the movement of a dial 326 by a user. Such a wick adjustment mechanism is described in detail in U.S. Patent Application Publication No. US 2003/0138241 A1, which is incorporated herein by reference. The diffused active material exits the diffuser through a chimney or vent 332 formed in the top of the housing 310.

A lighting element (not shown in FIGS. 11 and 12, but shown schematically at 390 in FIGS. 12A and 12B) of the diffuser 301 preferably comprises at least one LED, more preferably a plurality of LEDs. The LED(s) are disposed in the housing 310 beneath a cover 314. During operation, light from the LED(s) is emitted from the diffuser through one or more windows 334. The embodiment shown in FIG. 12 has a number of windows 334 formed in a back surface of the cover 314 and arranged in a fan shape. Additionally or alternatively, the cover 314 is preferably made of a translucent or transparent material so that light will be emitted through the entire cover 314.

The diffuser 301 shown in FIG. 11 includes a pair of LEDs, which shine through the windows 334, and preferably also through the cover 314 (if it is translucent). Light emitted from the windows 334 can be projected onto a wall W or other surface to form a lighted display or "wall wash" in the shape of the windows 334. Since two LEDs are used in the illustrated embodiment, two separate wall washes L1 and L2 are projected onto the wall W. Such a wall wash feature is possible by locating the diffuser 301 a short distance from a wall or other projecting surface. By using a corded arrangement as shown, the diffuser 301 can be readily placed in a desired location for viewing by a user, and can be positioned at a desired distance from the projecting surface to, for example, adjust the size of the projected image. Alternatively, the wall wash feature could also be applied to a plug-in device that plugs directly into a wall socket. In such an arrangement, the light would preferably project from a back surface of the diffuser onto the wall above the wall socket. Further, the wall wash feature may be generally applicable to a wide variety of lighting features. For example, any nightlight or lighted diffuser could be configured to create a wall wash on the wall to generate a decorative display. Moreover, the wall wash could be configured to move, by moving either the lighting element or the window through which the light shines, or varying the color and/or intensity of the lighting element, thereby creating a moving or changing projection. Sill further, the shape of the at least one window could be varied by, for example, providing interchangeable inserts or slides of varying shape, color, opacity, or the like, so as to allow a user to change the projected image by simply changing the insert. Control of the lighting elements could be accomplished by the provision of one or more light controllers to control the color and/or intensity of the LEDs, so as to produce a predetermined presentation. In particular, a programmable processor may be used to allow a user to program the operation of light the controller(s) to control at least one of the color and intensity of at least one of the plurality of light emitting diodes, to produce a desired presentation, over a set period, for instance. Suitable control options are described in more detail in the section entitled Diffuser with Coordinated Emission of Light, and/or Sound.

A pair of switches 322, 324 is provided on the diffuser 301. Preferably, these switches control operation of the LEDs 390. In particular, the first switch 322 preferably is used to select from among a plurality of color programs to change the color of light emitted from the diffuser, and the second switch 324 is preferably used to control the brightness or intensity of the LEDs. The switches 322, 324 could preferably be connected to one or more light controllers, such that when actuated by the respective switch, the light controller controls the color and/or intensity of the LESs, as described in more detail below in the section entitled Diffuser with Coordinated Emission of, Light, and/or Sound. Alternatively, each of the buttons 322, 324 could be used to control a different one of the LEDs 390, such that each LED can be separately turned on and off manually by pressing the button associate with that LED. The circuit diagram of FIG. 12B is representative of this configuration. In another alternative, switch 322 could be used to control operation of the heating element 308 and switch 324 could be used to control operation of both of the LEDs 390. The circuit diagram of FIG. 12A is representative of this configuration. Of course any number of different switches could be used to control different functions, depending on the specific configuration of the diffuser.

FIGS. 13 and 14 show a diffuser according to the docking station variation of the remote-use embodiment. A diffuser 401 according to this embodiment comprises a multi-piece housing 410 (having a front portion 410a and a back portion 410b), a container 450 of active material, a heating element 408 (not shown), and a plug 412, which are similar to those described above with respect to the shine-through embodiment. Accordingly, details of the construction of those elements are omitted. In addition, the diffuser 401 of this embodiment comprises a remote-use assembly, including a docking station 460 that releasably holds the diffuser 401 during use, and a cord 442 that transmits electrical energy from the wall socket S to the docking station to power the diffuser 401.

One end of the cord 442 has a wall plug (not shown) that plugs directly into a wall socket S, and the other end of the cord 442 is connected to the docking station 460. The docking station releasably holds the diffuser 401 during use and provides electrical energy, via the cord 442, to the diffuser 401 from the remote wall socket S. The docking station 460 comprises a cradle portion 464 for receiving and supporting the diffuser, and a back portion 462 having a receptacle 466 for receipt of the plug 412 of the diffuser 401. Preferably, as shown in FIG. 14, the receptacle 466 is a standard electrical outlet. However, the receptacle need not be a standard electrical outlet and could be configured as any other suitable type of receptacle.

While not shown, this variation of the remote-use embodiment could also include a transformer/rectifier for converting alternating current from the wall socket S to direct current, with the cord 442 transmitting the direct current to the receptacle 466 of the docking station 460 to power the diffuser 401.

A lighting element (not shown) of the diffuser 401, preferably comprises at least one LED, more preferably a plurality of LEDs. The LED(s) are disposed in the housing 410 beneath a cover 414. During operation, light from the LED(s) is emitted from the diffuser through a window 434. The window 434 is formed in a back surface of the back portion 410b of the housing 410. Additionally or alternatively, the cover 414 can be made of a translucent or transparent material so that light will be emitted through the entire cover 414. While the window 434 of this embodiment is depicted as simply a curved panel of transparent or translucent material, the window 434 may, of course, be formed in any desired shape or pattern, so as to produce a wall wash similar to that produced by the diffuser of FIG. 11.

Buttons or switches 422 and 424 are provided on the diffuser 401, and can be used for any of the functions disclosed with respect to the switches 322, 324 in the direct-corded embodiment of FIG. 11. Accordingly, a detailed description of the operation of the switches 422, 424 has been omitted.

Of course, since the docking station 460 preferably includes a standard electrical outlet as the receptacle 466, it could advantageously be used with any conventional plug-in diffuser. Thus, the docking station 460 may also be used to retrofit existing diffusers to be used in locations remote from a wall socket.

Alternatively, the remote-use embodiments may preferably include one of many types of lock-and-key arrangements. For example, the docking station and/or the diffuser could be provided with one or more mechanical features that are specially designed to mate with the other of the diffuser and the docking station of our invention, but are so configured as to prevent use of the docking station and/or diffuser with unapproved devices. Further, the lock-and-key arrangement could be realized by providing the diffuser with one of an identification tag and a tag reader (such as, for example, a radio frequency identification tag and tag reader, respectively), and providing the docking station with the other of the tag and the tag reader, whereby the combination of a diffuser and a docking station will not work unless the proper ID tag is read.

Diffuser with Coordinated Emission of Fragrance, Light, and/or Sound

In yet another aspect, illustrated in FIGS. 15-19, our invention relates to a diffuser, wherein the emission of fragrance, light, and/or sound is controlled in a coordinated manner. Details of this feature are described in terms of a single presentation unit in PCT International Patent Application No. PCT/US03/14769 (the '769 application"), filed May 13, 2003, and entitled Coordinated Emission of Fragrance, Light, and Sound, which is incorporated herein by reference. This feature can be advantageously adapted for use with any of the foregoing embodiments and variations of our invention. In addition, the coordinated emission feature may be used in connection with a diffuser having an acoustic generator for generating ambient sounds or music. Acoustic generators for generating sound and/or playing sounds/music stored in a memory are known in the art. These can be found in conventional clock radios, such as described in U.S. Pat. No. 5,483, 689. Other examples of acoustic generators may be found in U.S. Pat. Nos. 5,452,270 and 6,423,892.

For convenience, this aspect of our invention will be described with respect to a diffuser that emits light, fragrance, and sound. However, it should be understood that our invention applies equally to diffusers that emit either light or sound in coordination with fragrance, as well as to other presentation units having light and sound but not fragrance. While a diffuser according to this embodiment of our invention could be configured as a plug-in device, due to the increased size of a unit including light, fragrance, and sound emitters, as well as the control circuitry, the diffuser is preferably a "table-top" unit, which can be located on any suitable supporting surface (e.g., floor, table, desk, stand, etc.). Thus, this embodiment may advantageously incorporate the features of the remote-use assembly embodiment described above. Alternatively, the unit might be provided with a conventional fixed electrical cord for connection with a wall socket, or might be battery powered.

Figure 15:
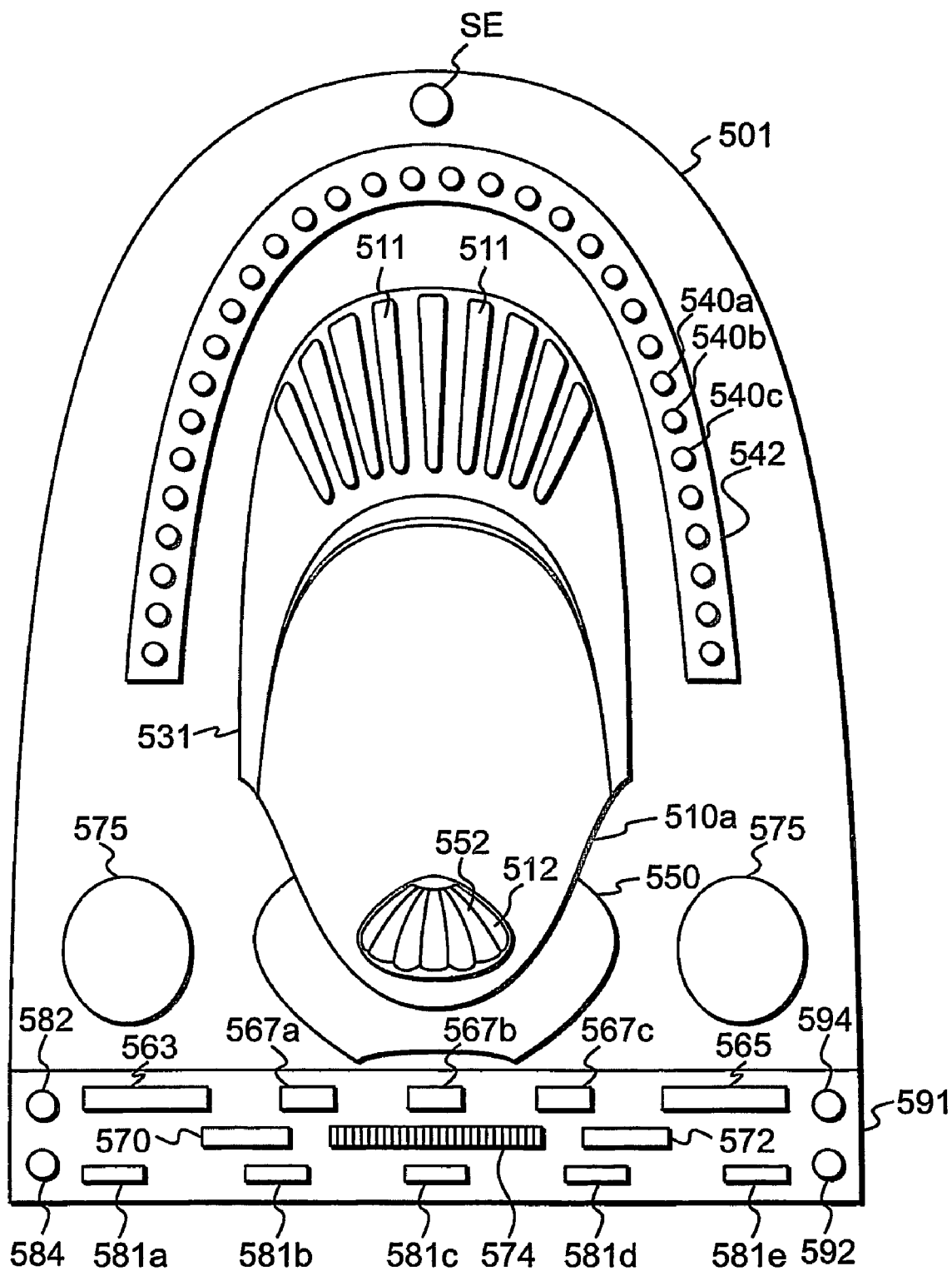
FIG. 15 is a front view of a diffuser according to another embodiment our invention.

FIG. 15 shows an embodiment of our invention in which a single diffuser 501 emits light, fragrance, and sound. The diffuser 501 includes a light array 542 including a plurality of different color LEDs. In particular, light array 542 includes a plurality of red LEDs 540a, blue LEDs 540b, and green LEDs 540c. The plurality of LEDs can be individually activated and controlled to adjust their respective colors and intensities. Of course, any number of different color LEDs may be provided to produce the desired light show. For simplicity sake, our invention will most often be described using a three-color arrangement. Also, other types of light emitting devices may be substituted, as desired.

Diffuser 501 also includes a fragrance dispenser 531 for dispensing fragrance. The dispenser 531 releasably holds a container 550 of active material, preferably a bottle of liquid active material. Of course, the diffuser 501 of this embodiment could be adapted for use with any other variety of active material or container disclosed herein. A raised pattern 554 on the side of the container 550 aligns with an opening 512 in a front shell 510a of dispenser 531. The raised pattern 554 and the opening 512 mate to cause the container 550 to be retained in a cavity defined by the front shell 510a, so that the container 550 may dispense fragrance. Vents 511 may be provided to allow the passage of air across a dispensing wick (not shown) for wicking liquid from the container 550 to the air. The passage of air though the vents 511 may be aided by a fan, if desired. The details of the operation of fragrance dispensers such as dispenser 531 are readily known by those of skill in the art.

Diffuser 501 also includes speakers 575 for emitting music, sounds of nature, and the like, to produce a suitable effect in connection with a light presentation by light array 542 and an aroma released from the liquid in container 550.

A programmable user control 591 is also provided to program the operation of light array 542, speakers 575, and fragrance dispenser 531. The user control 591 includes an on/off switch 592 which activates each of light array 542, speakers 575, and fragrance dispenser 531. Thus activated, the light array 542 sends power to the LEDs 540a-540c to produce light, speakers 575 to emit sound, and fragrance dispenser 531 to emit the fragrance from the liquid in container 550. The manner in which each of these systems is operated can be programmed from user control 591.

Buttons 581a-581e activate preprogrammed presentations stored in a memory to cause a processor to control each of the light array 542, speakers 575, and fragrance dispenser 531 to produce a coordinated presentation of light, sound, and aroma. Such presentations may include varying the activation, color, and intensity of LEDs 540a-540c over the course of the presentation; setting and/or varying the rate at which fragrance is dispensed from dispenser 531 over the course of the presentation; and playing a designated audio presentation through the speakers 575 over the course of the presentation.

The predetermined presentation may also be activated automatically in response to a signal from a sensor SE. The sensor SE may be any one of a number of sensing devices. For instance, the sensor SE may be a photosensor that detects light. Accordingly, the sensor SE may be set such that, when a predetermined amount of light is detected (indicating, for instance, sunset or sunrise, a room light being turned on or off, or the like), the sensor causes diffuser 501 to activate one of the preprogrammed presentations stored in the memory. Other examples of suitable sensors include sensors that detect temperature, sound, movement, fragrance (i.e., a feedback loop), etc. Also, the operation and configuration of a sensing system may be made in accordance with any conventional practice.

Alternatively, a user may program diffuser 501 to produce a personalized presentation. Pressing button 563 allows a user to program the fragrance aspect of the presentation. Once button 563 has been pressed, the user can press button 582 to determine the starting rate of fragrance emission. The starting rate is set by pressing button 570 to reduce the fragrance emission rate and pressing button 572 to increase the rate. The selected rate is displayed on display 574. Once the starting rate is set, the user may press button 584 to choose an ending rate for the fragrance emission in a manner similar to that for setting the starting rate. Once set, the dispenser 531 will alter the rate of emission of fragrance over the course of the presentation from the set starting rate to the set ending rate.

By pressing buttons 567a, 567b, and 567c, a user can set the intensity of the red LEDs 540a, blue LEDs 540b, and green LEDs 540c, respectively. For instance, by pressing button 567a, the user can set the intensity of the red LEDs 540a by first pressing button 582 to set the beginning intensity and then pressing button 584 to set an ending intensity. The intensities can be adjusted during setting using buttons 570 and 572 to adjust the intensities down and up, respectively. Once set, the light array 542 will adjust the intensities of LEDs 540a-540c over the course of the presentation.

Button 565 may be pressed to set the sound to be emitted from speakers 575. Once button 565 has been pressed, the user may press any one of buttons 581a-581e to select from different available sounds stored in a memory of diffuser 501. The user may also set a starting volume for the chosen sound by pressing button 582 and then adjusting the volume using buttons 570 and 572 to decrease or increase, respectively, the starting volume. The ending volume may be set in a similar manner by pressing button 584 and then setting the volume again using buttons 570 and 572.

Once all of the desired settings have been programmed by the user, the user may press button 594 to begin the coordinated presentation. The duration of the presentation may be adjusted by the number of times the user presses button 594. For instance, the user may press the button once to begin a fifteen-minute presentation, but press the button twice to cause diffuser 501 to implement the programmed presentation over a thirty-minute period.

Of course, the user may set only one of the light array 542, speakers 575, and fragrance dispenser 531, or combinations thereof to produce the desired effect. Also, FIG. 15 merely shows one potential embodiment of our invention. More complicated and involved programming systems may be provided to give the user enhanced control of the system. Also, the user may also be allowed to load personalized audio files or other formats to play specified sounds. For instance, the speakers 575 could be used to play music provided from a radio, CD player, tape cassette, MP3 player, and the like using means well known in the art.

Figure 16:
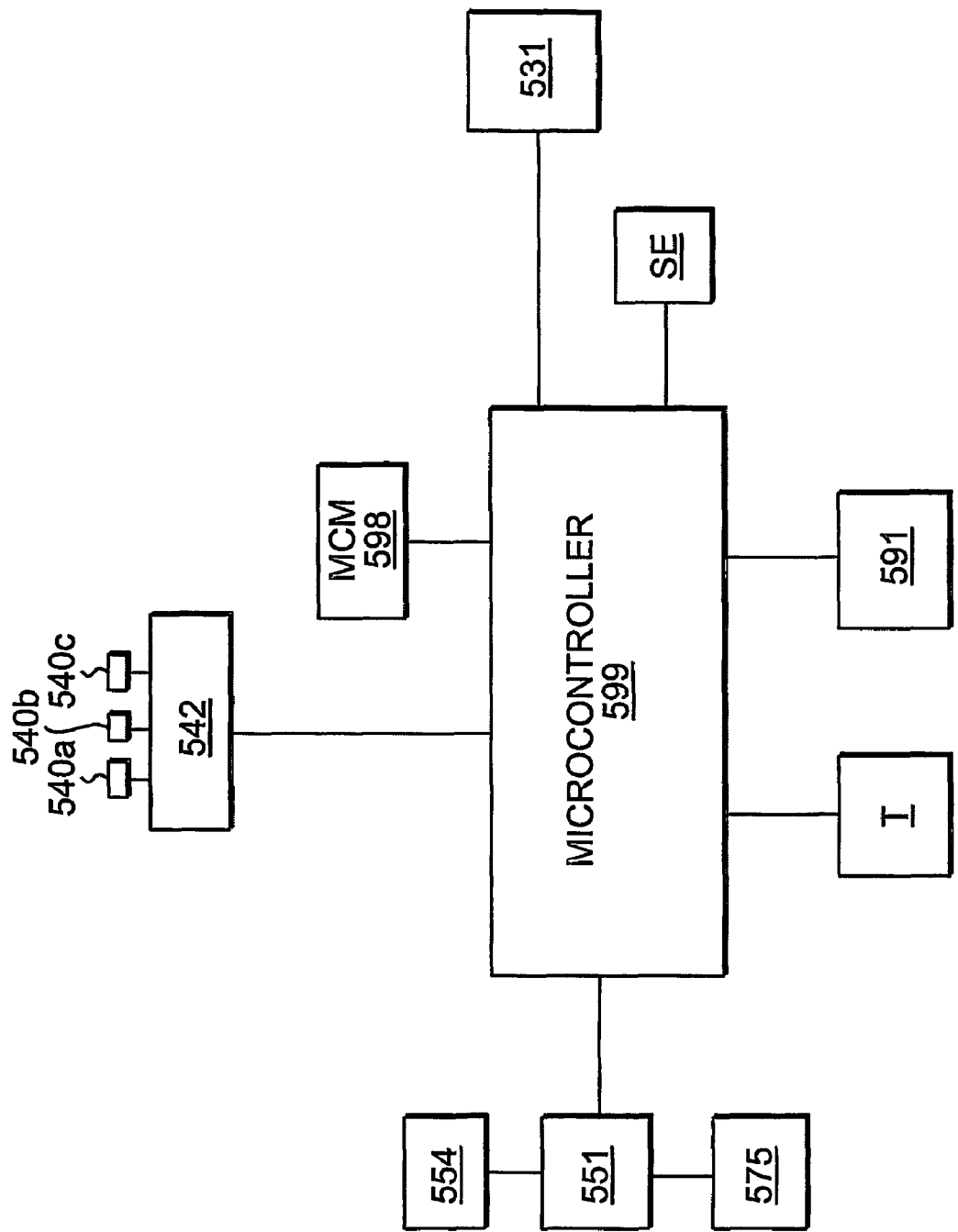
FIG. 16 is a diagrammatic plan view showing the arrangement of the components of the diffuser of FIG. 15.

FIG. 16 shows a diagrammatic representation of functional units of diffuser 501. Microcontroller 599 is a programmable controller that produces output signals to control the emission of light from the LEDs of light array 542, the sounds emitted from speakers 575 of an audio system 551, and the amount of fragrance emitted from fragrance dispenser 531. Microcontroller 599 produces and outputs the signals to operate these devices according one or more programs stored in the memory 598. The signals may be in the form of voltages, coded pulses, or other coded signals, which control the operation of the various components. The programs may be preset in the memory 598 and then selected and activated by a user through user control 591. Alternatively, a user may program a personalized program for controlling diffuser 501 using user control 591 and store the program in memory 598, in the manner described above, such that microcontroller 599 produces the same over the course of the user programmed presentation.

In running a set program stored in the memory 598, the microcontroller 599 may cause audio system 551 to play audio files stored in memory 554 through speakers 575. Also, memory 554 may be removed, in which case, memory 598 can serve the same functions of memory 554, depending on preferred design considerations.

Operation of microcontroller 599 can also be activated to produce a presentation according to a program stored in memory 598 by a signal from sensor SE, as discussed above.

In addition, diffuser 501 may include a timing mechanism T. The timing mechanism T may be an oscillator, crystal, conventional clock, etc. The timing mechanism T controls the operation of microcontroller 599 in accordance with the program from the memory 599. In addition, the timing mechanism T may be used to control the length of a presentation of light, sound, and fragrance set by a program in memory 598, as programmed through user control 591. In addition, in alternative embodiments, a user may use the user control 591 to set the time at which a particular presentation stored in the memory 598 will begin.

As discussed above, the various components for emitting light, sound, and fragrance may be configured to work in coordination with each other in any one of a number of ways, as would be appreciated by one of ordinary skill in the art. The same is true for implementing the control and programming of the various components. A description of the preferred control and programming of the components is described below.

Figure 17:
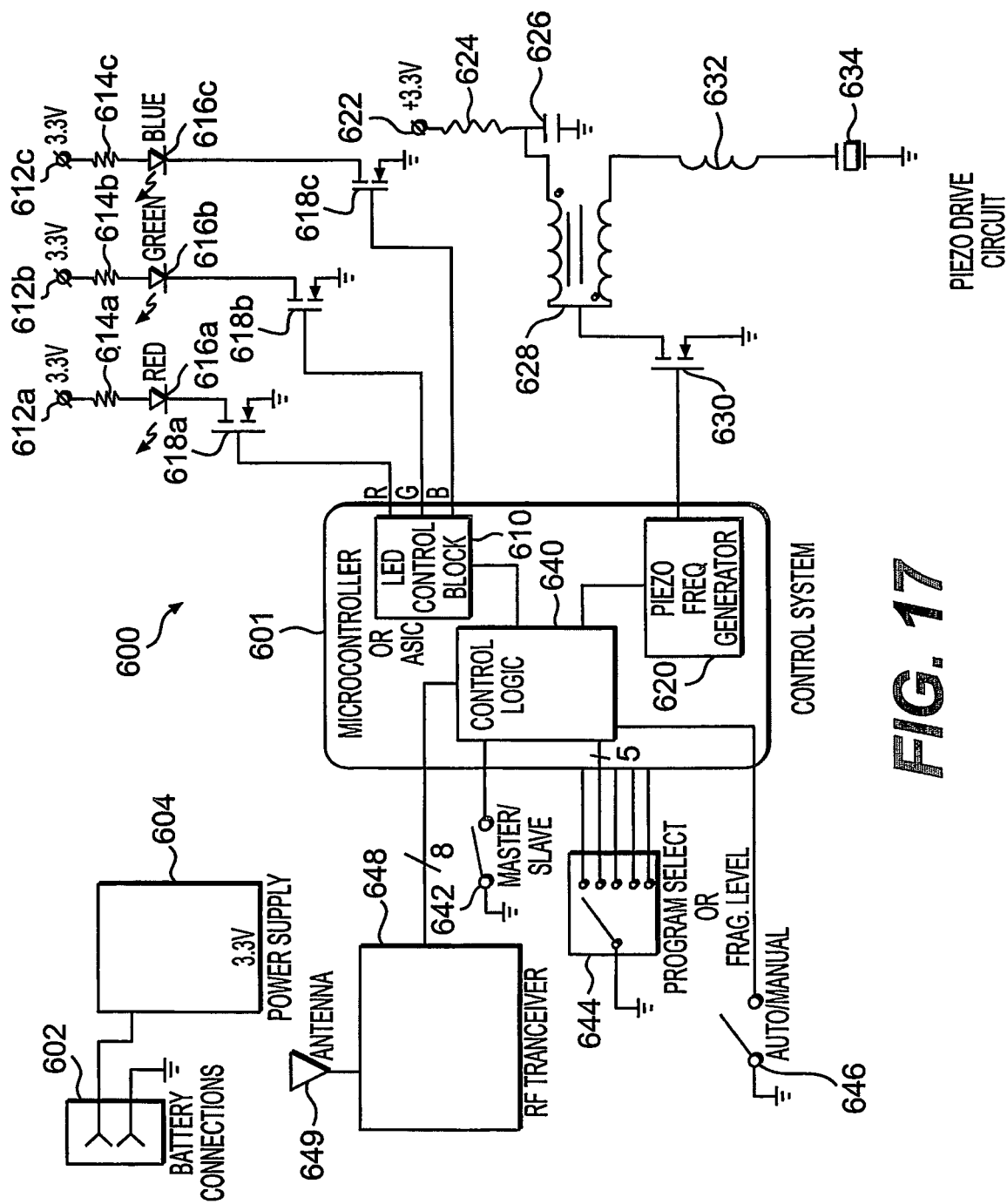
FIG. 17 is a diagram of a circuit used for controlling the operation of one embodiment of our invention.

As described above, the term diffuser includes piezoelectric devices. This embodiment will be described with respect to such a piezoelectric device, for exemplary purposes. Generally, piezoelectric diffusers can use the same cartridges as other diffusers, such as evaporative diffusers. The only difference is the piezoelectric pump used to dispense the fragrance, as is known in the art and described in, for example, U.S. Pat. No. 6,450,419. FIG. 17 shows a circuit diagram of one preferred control arrangement for operating a diffuser 600 that produces a coordinated/combined presentation of light and fragrance. The circuit diagram is directed to a diffuser having a piezoelectric atomizing fragrance emitting device. Of course, the circuit could be readily modified by one of ordinary skill in the art to be used in connection with another type of fragrance emitting device, such as the evaporative-type device discussed with respect to the foregoing embodiments, with or without a fan, heater, or other evaporation enhancing features. The presentation device is powered by a battery 602; however, other sources of power, such as an AC current source may be also be used. A power supply 604 draws power from the battery 602 and then supplies 3.3 volts to the presentation device. In other embodiments, the current level (or voltage level) used may be altered, as desired or as necessary for the components to be powered.

A microcontroller (or ASIC) 601 controls the operation of the diffuser 600, and is powered by power supply 604. Microcontroller 601 includes a control logic 640 that provides the operational instructions to the various elements of the diffuser 600 in accordance with input signals or internal programs. The control logic 640 converts received signals or runs internal software routines to set the operation of the various elements, including an array of LEDs and a fragrance dispenser.

The control logic 640 sends a signal for controlling the operation of the array of LEDs to LED control block 610. When using pulse width modulation to drive and control the LED array, the LED control block 610 sets the duty cycles for the LEDs based on the instruction from the control logic 640.

Supply lines 612a-612c supply 3.3 volts across resistors 614a-614c, from power supply 604. Resistors 614a-614c in turn power a red LED 616a, a green LED 616b, and a blue LED 616c, respectively. Field effect transistors (FETs) 618a-618c are turned on and off in accordance with the respective duty cycles generated by the LED control block 610. Operation of the FETs 618a-618c control the LEDs 616a-616c to be activated for the portions of the duty cycle set by the LED control block 610. Thus, the intensity and color of the LEDs 616a-616c can be varied to produce the desired effects. Typically, pulse width modulation is used to control a constant current to be applied to a given diode for a set period of one duty cycle, thus controlling the total current applied to the LED over the full duty cycle. Thus, the diode flickers on for the set portion of each duty cycle, and off for the remainder of the duty cycle. Of course, this on and off operation is so fast (a typical duty cycle is in the range of a few milliseconds) that the color and intensity of the diode appears constant to an observer (with no discernable flicker), until the set period of activation over the duty cycle is changed.

While three LEDs are shown with respect to this embodiment, any number of LEDs may be used. In addition, the choice of which color LEDs to provide may be dictated by design preferences. The intensity and exact color of the LEDs may be varied by changing the current applied to each diode.

When three colors of LEDs are used, typically mixtures of red, green, and blue LEDs are preferred. Generally, one of each color LED will be provided in close proximity to one of each other color. With such an arrangement, the exact color of each diode of the set of three different colors can be adjusted to create a blended color, for example, amber or purple. This blending can be achieved by providing the three diodes in such close proximity that the observer only sees the blend of colored lights, rather than each individual diode. Alternatively, or in addition, a light diffuser may be provided to diffuse the light of the three diodes to produce the combined color. In other embodiments, the lights may be projected off of a surface to be combined before being viewed by an observer.

LEDs of a wide array of colors are readily available from lighting manufactures. Also, the arrangement and operation of LEDs to achieve a desired presentation would be apparent to one of ordinary skill. Accordingly, a detailed description of specific LEDs and configurations which can be used with our invention is unnecessary.

A piezo frequency generator 620 controls the operation of a fragrance dispenser, which, in this case, is a piezoelectrically actuated atomization device, such as those known and described in detail in, for example, U.S. Pat. Nos. 6,292,196 and 6,341,732. The atomization device typically operates to atomize fragrance for an approximately eleven-msec burst at set intervals. The piezo frequency generator 620 controls the frequency of the eleven-msec bursts to adjust the rate at which the fragrance is dispensed (thus, controlling the potency of the aroma). Again, typically, the piezo frequency generator 620 will operate using pulse width modulation.

A supply line 622 provides power from power supply 604 across resistor 624. The power is supplied across resistor 624 to a capacitor 626, causing the voltage stored in the capacitor 626 to rise to 3.3 volts, at which point the power flow to the capacitor 626 stops and the capacitor 626 supplies current through transformer 628 to ground, charging the transformer 628. A pulse from the piezo frequency generator 620, set in accordance with the instructions from the control logic 640, controls the FET 630 to open and close. When FET 630 is closed, the current from transformer 628 is pushed through inductor 632, which smooths the current from a square wave to a sine-like wave. The current then passes to a piezo 634, causing the device to vibrate and to release a puff of fragrance, as discussed above.

The control logic 640 may be programmed/controlled in any number of ways. The control logic 640 may first be controlled via a master/slave switch 642. When switch 642 is set in the slave position, control logic 640 is provided with external signals for setting operation of the diffusers 600. For instance, if a plurality of individual diffusers 600 are being used together, one can be designated a master, and the rest slaves. Of course, such an embodiment is only one possible configuration of our invention and is not necessary to realize the benefits of our invention. If only one diffuser 600 is used, the following description of the master/slave circuitry can be dispensed with. In such a case, the diffuser 600 would be controlled along the lines described hereinafter with reference to the master unit.

The slave devices receive signals from the master dictating the operation of each slave. The signals may be provided from the master to the slaves through any one of a number of systems, including infrared signals, hard-wired connections, radio signals, and the like. In the control embodiment shown in FIG. 17, an RF transceiver 648 is provided to send and to receive radio signals. Alternatively, the master device may be a remote control, rather than another diffuser 600.

When switch 642 is in the slave position, the RF transceiver 648 receives an external signal, through an antenna 649, from a remote control, a master-designated diffuser 600, or the like. That signal is transmitted from the RF transceiver 648 to control logic 640 to set the presentation of light and sound through the LED control block 610 and the piezo frequency generator 620. When switch 642 is in the master position, the operation of the control logic is set by an internal program at this diffuser 600, such that microcontroller 601 acts as the master. In this case, the operational program from control logic 640 is sent to the RF transceiver 648 and broadcast to slave devices via the antenna 649.

Alternatively, an auto/manual switch 646 may be operated to override a slave designation by switch 642 or a set internal program to allow a user to manually set the fragrance output and light show. In this case, a program select switch 644 may be operated by a user to set a light show program for the LEDs 616a-616c, a fragrance level to be dispensed by the operation of the piezo 634, or a combination thereof.

Figure 18:
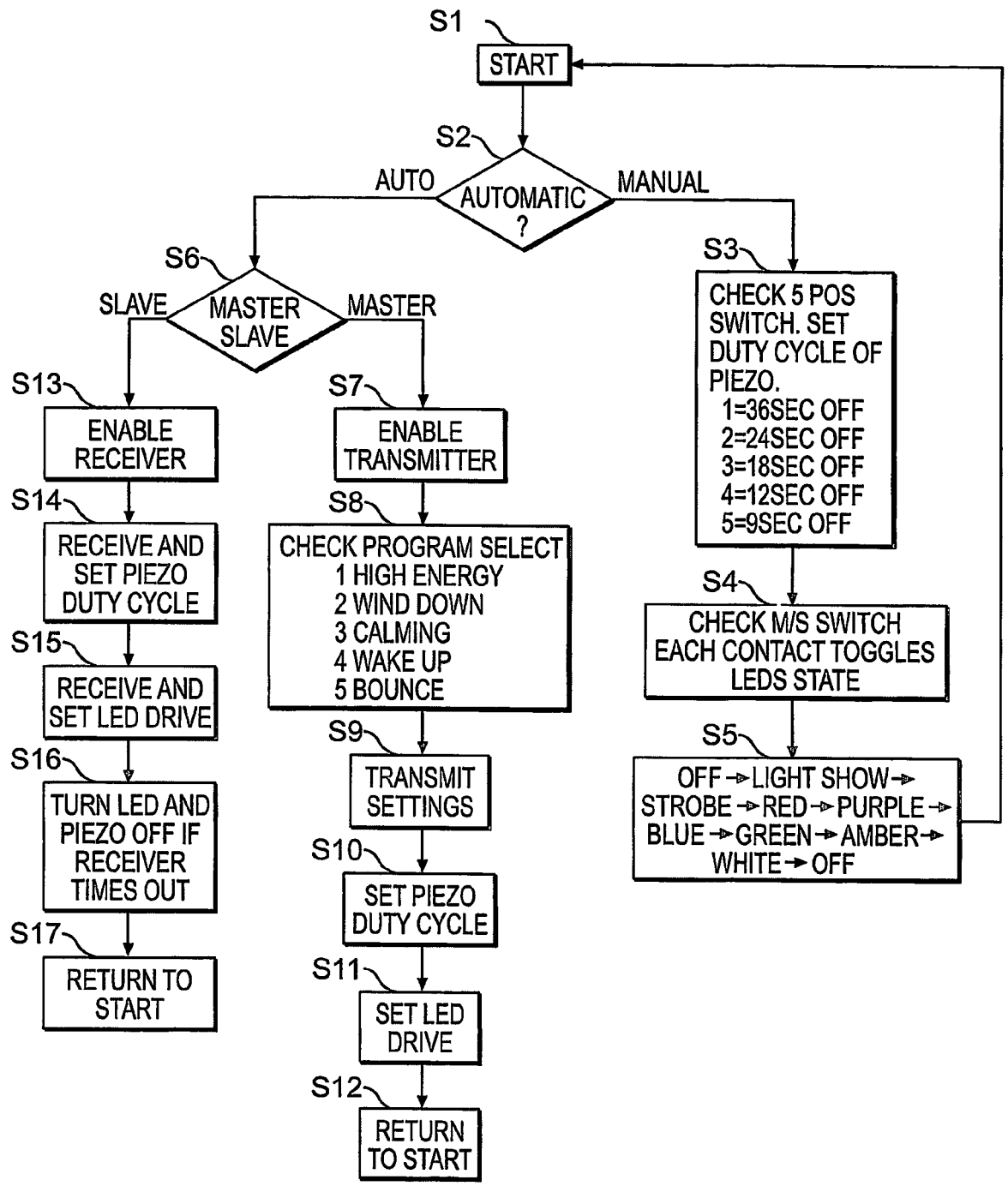
FIG. 18 is a flow chart showing the operation of a program for controlling the circuit shown in FIG. 17.

FIG. 18 shows one potential program for operating the control system shown in FIG. 17. Again, however, this is only one way of implementing control of an embodiment of our invention. One of ordinary skill in the art will appreciate that a wide variety of programs may be implemented to produce the desired control over the presentation of coordinated light and aroma.

The program starts operation of the device at step S1. At step S2, it is determined whether operation of the microcontroller 601 is to be set manually by a user or automatically with a set program. If manual operation is selected, the program proceeds to step S3. In step S3, the setting of the five-position switch 644 is checked to set the duty cycle for operating the piezo 634. For instance, in a first switch setting, the piezo 634 is activated to release fragrance every thirty-six seconds; in a second switch setting, the piezo 634 is activated to release fragrance every twenty-four seconds; in a third switch setting, the piezo 634 is activated to release fragrance every eighteen seconds; in a fourth switch setting, the piezo 634 is activated to release fragrance every twelve seconds; and in a fifth switch setting, the piezo 634 is activated to release fragrance every nine seconds. In step S4, the operation of the master/slave switch 642 is checked. The system is set such that different preprogrammed light shows are selected depending on how many times a user toggles the switch 642. Step S5 sets the light show from among an off setting, a variant light show, a strobe setting, emission of red light, emission of purple light, emission of blue light, emission of amber light, and emission of white light, depending on the toggling of switch 642.

If the automatic mode is set in step S2, the program proceeds to step S6, in which it is determined whether the microcontroller 601 is set as a master or a slave. If it is set as a master, the program proceeds to step S7 to enable the RF transceiver to transmit the program to slave devices. In step S8, a program selection is checked from among five different programs to be selected. The five programs may be selected by setting switch 644. The different programs include a Ahigh energy@ program in which the piezo 634 is set to emit fragrance every nine seconds and the LEDs perform a programmed light show. A "wind down" program sets the fragrance device to decrease from a high setting to a low setting over a two hour period, and sets the LEDs to change from emission of white light of a high intensity to emission of blue light of a low intensity, also over a two hour period. A "calming" program begins with a low fragrance emission rate and a blue light, and varies the intensity of both over the course of a thirty-minute cycle. A "wake-up" program changes from a low fragrance intensity to a high fragrance intensity, and from a low intensity blue light to a high intensity white light, over a forty-five-minute period. Also, in the "wake-up" program, the intensities (fragrance and light) and colors of a master and slave device proceed in inverse relation to each other over the course of the presentation. So, as the color emitted from the LEDs of the master changes from white to blue, the color in the slave changes from blue to white. A "bounce" program causes a master device to emit purple light and a medium level of fragrance for fifteen minutes while the slave devices are shut down. After the fifteen minutes, the master shuts down and a slave device emits the purple light and medium level of fragrance. The "bounce" program continues by causing a different device in the master-slave system to activate every fifteen minutes, with the other devices lying dormant.

Of course, a user can adjust the operation of the program by setting switch 642 in the master position, setting switch 646 in the manual position, and setting a desired fragrance level and a desired lighting scheme with switch 644.

In step S9, the set program is transmitted to RF transceiver 648 to be sent to the slave devices, and LED control block 610 and piezo frequency generator 620, to set the presentation. In step S10, the piezo duty cycle is set in piezo frequency generator 620. In step S11, the LED duty cycles are set in LED control block 610, based on the set presentation. In step S12, if the presentation has timed out, the program returns to the start at S1. If the slave setting is set at step S6, the program proceeds to step S13, in which RF transceiver 648 is enabled to receive a signal from a master device. In step S14, the piezo frequency generator 620 sets a duty cycle in accordance with a signal received from the master device. In step S15, the LED control block 610 sets duty cycles for the LEDs based on the received signal from the master device. In step S16, the piezo frequency generator 620 and LED control block 610 turn off if the RF transceiver 448 times out. In step S17, the program returns to the start.

Figure 19:
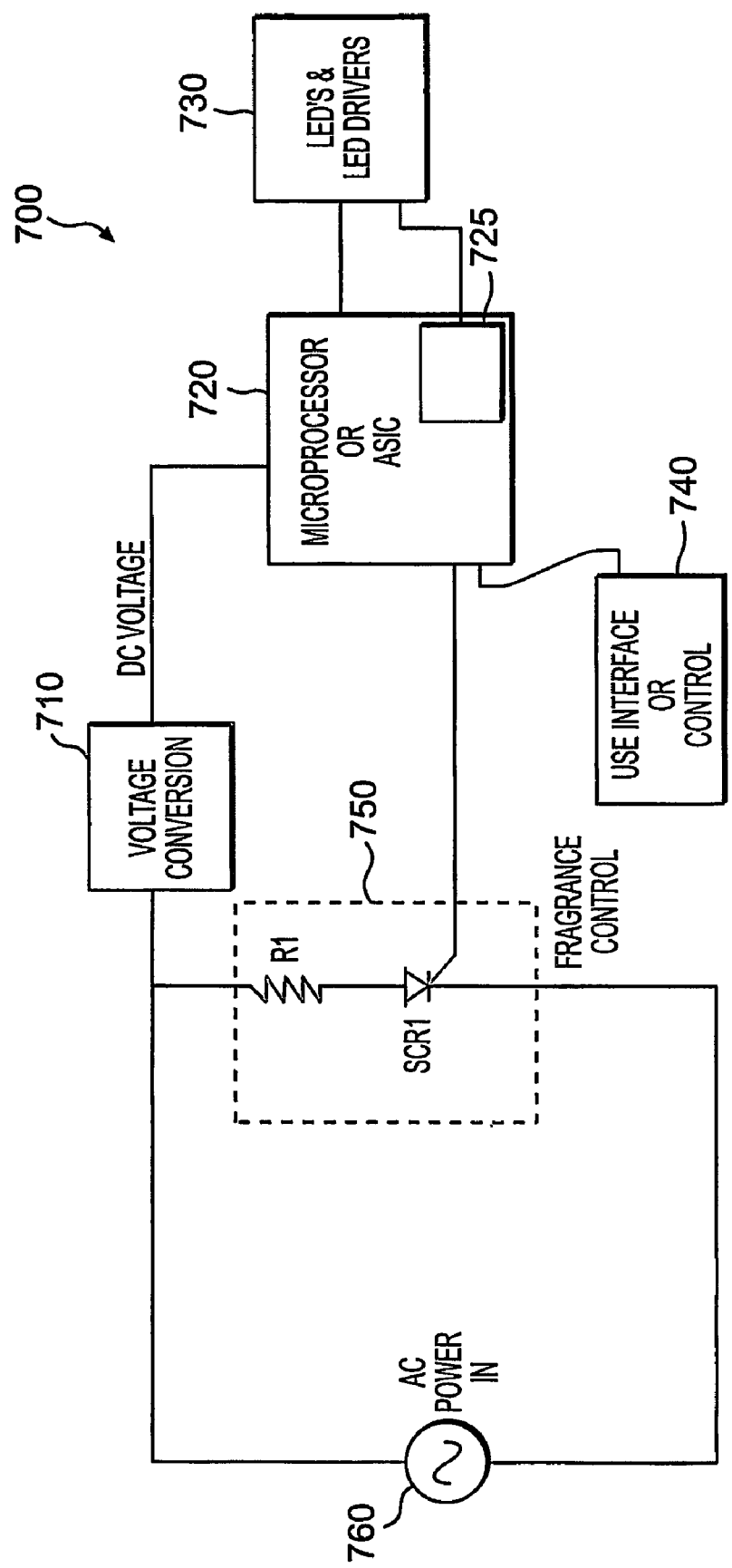
FIG. 19 is a diagram of another circuit for controlling the operation of another embodiment of our invention.

FIG. 19 shows a circuit diagram of yet another control system for operating a somewhat less complex diffuser according to our invention. The diffuser of this embodiment is preferably an evaporative diffuser having an LED light source, such as the diffuser with LED nightlight or the diffuser with shine-through feature described above. In this embodiment, power is supplied to the system 700 through an AC power source 760. However, battery power could be used in the place of plug-in AC power sources. A voltage conversion device 710 converts the AC voltage from the AC power source 760 to a DC voltage. A microprocessor 720 receives power from voltage conversion device 710 and controls the operation of system 700 using the received power. The microprocessor 720 is controlled by user interface/control 740 (or perhaps a sensor feedback) in any number of ways, including internal programs, user input, etc., as explained in more detail above.

Based on a control program from the user interface/control 740, the microprocessor 720 sends a program signal to LED drivers 730. The LED drivers 730, in turn, control a plurality of LEDs to produce a light show, as also discussed in more detail above. The microprocessor 720 also sends a control signal to fragrance control 750. In this embodiment, the fragrance dispenser being controlled is an evaporative-type dispenser. A resistor R1 is heated by a current passing across the resistor R1. Typically, the resistor R1 is placed adjacent an area at which a fragrance-containing gel or oil is exposed to air and the heat from the resistor R1 causes the fragrance to be vaporized. A switch SCR1 varies the current passing across the resistor R1, thus varying the heat produced by resistor R1 and the rate of vaporization of the fragrance. In alternative embodiments, instead of, or in addition to the resistor R1 a fan which is controlled by switch SCR1, or an atomization device may be used. Also, switch SCR1 may be replaced by an FET in other embodiments.

Microprocessor 720 may also control a use-up cue 725. The use-up cue 725 tracks the use of fragrance control 750 to estimate the time at which the fragrance in the fragrance dispenser is likely to be used up. When the use-up cue 725 determines that fragrance has been spent, it sends a signal to LED drivers 730 to cause the LEDs to illuminate in a pattern, color, or other manner to indicate to a user that it is time to refill or replace a fragrance in the fragrance dispenser.

Again, however, FIG. 19 shows only one possible arrangement for configuring and controlling a device according to our invention. In addition, separate from the specifics of the method for providing control of the system, a plurality of fragrance dispensers may be provided, as well as an audio system. The control logic of a processor used to control a device according to our invention may be suitably modified to account for and control these additional devices, as necessary.

While the foregoing embodiments are generally directed to diffusers that draw power from an electrical wall socket, each of the various embodiments could be adapted to be powered by batteries or a battery pack. This would allow even more flexibility in the placement of diffusers. Preferably the battery power source would be rechargeable for repeated use. In such an application, the remote-use embodiments described above could be adapted to serve as charging stations for battery-powered diffusers, instead of serving as a constant power source for the diffusers.

Various preferred embodiments of our invention have been disclosed herein. While in some instances these embodiments are disclosed individually, it should be understood that the features and advantages of each could be used alone or in combination with one another. For example, a device according to our invention may include any combination of one or more of a diffuser (including any of the various diffusers discussed herein), an LED nightlight, a shine-through feature, a remote-use assembly (either with or without a docking station or transformer), and a coordinated emission of light, fragrance, and/or sound.

In addition, a device according to our invention may include various other features that enhance or compliment the visual, aural, or fragrant aspects of our invention, such as, for example a fan, an adjustment mechanism for adjusting the rate of diffusion of an active material, louvers, and/or vents. Diffusers having such features are known in the art and are disclosed in, for example, the '241 publication. It should be understood that any of the embodiments disclosed herein could be readily adapted to include these or other performance enhancing features.

While the present invention has been described with respect to what is at present considered to be the preferred embodiments, it is to be understood that the invention is not to be limited to the disclosed embodiments. To the contrary, the invention is intended to cover various modifications and equivalent arrangements within the spirit and scope of the appended claims. The scope of the following claims is to be accorded the broadest interpretation so as to encompass all such modifications and equivalent formulations and functions. The diffuser of the present invention may be manufactured of commonly available materials, and may utilize readily available replacement cartridges in the operation thereof. The individual electrical elements employed are commonly available and known to one skilled in the art, although not in the configuration and arrangement of the present invention.

INDUSTRIAL APPLICABILITY

Our invention makes advances in diffusers having emission of light, fragrance, and/or sound. In particular, the invention provides for control of light, fragrance, and/or sound in a coordinated manner, thereby to achieve an overall desired effect in the condition of the area.

We claim:
1. An electrically operated diffuser, comprising:
a housing having a compartment for receiving an active material;
a plug disposed on said housing for connection of the diffuser to a power source;
a heating element located in proximity to the compartment of said housing, to heat an active material received in the compartment; and
at least one light emitting diode disposed in said housing and serving as a light,
wherein said heating element and said at least one light emitting diode are electrically connected to said plug, and
wherein a combined power consumption of said heating element and said at least one light emitting diode is at most two watts.

2. An electrically operated diffuser according to claim 1, wherein said at least one light emitting diode is electrically connected to said plug via a full-wave bridge circuit.

3. An electrically operated diffuser according to claim 1, further comprising an actuator switch for selectively activating said at least one light emitting diode to illuminate.

4. An electrically operated diffuser according to claim 1, further comprising a transparent lens at least partially enclosing said at least one light emitting diode and providing an even light dispersion.

5. An electrically operated diffuser according to claim 1, wherein said heating element is a resistance heater.

6. An electrically operated diffuser according to claim 1, further comprising an outlet formed in said housing for reception of a plug of an additional electrical appliance.

7. An electrically operated diffuser according to claim 1, wherein said at least one light emitting diode has a luminous intensity rating of at least about 5000 mcd at 20 mA.

8. An electrically operated diffuser according to claim 1, wherein when activated, said at least one light emitting diode provides minimal heat to an active material received in the compartment of said housing.

9. An electrically operated diffuser according to claim 1, wherein said at least one light emitting diode serves as a nightlight.

10. An electrically operated diffuser according to claim 1, wherein said at least one light emitting diode comprises a plurality of light emitting diodes.

11. An electrically operated diffuser according to claim 10, wherein said plurality of light emitting diodes comprises light emitting diodes of at least two different colors.

12. An electrically operated diffuser according to claim 11, further comprising a light controller for controlling the operation of said plurality of light emitting diodes.

13. An electrically operated diffuser according to claim 12, further comprising a fragrance controller for adjusting the rate at which the active material is diffused.

14. An electrically operated diffuser according to claim 13, wherein said fragrance controller and said light controller communicate so as to work in synchronization with each other.

15. An electrically operated diffuser according to claim 13, further comprising a processor for controlling the operation of said light controller to produce a predetermined presentation.

16. An electrically operated diffuser according to claim 15, further comprising a processor for controlling the operation of said fragrance controller to produce a predetermined presentation.

17. An electrically operated diffuser according to claim 16, wherein the predetermined presentation comprises at least one of (i) varying the rate at which the active material is diffused over the course of the presentation, and (ii) varying at least one of the color and intensity of at least one of said plurality of light emitting diodes over the course of the presentation.

18. An electrically operated diffuser according to claim 13, further comprising a programmable processor that allows a user to program the operation of the fragrance controller and light controller to control at least one of (i) the rate at which the active material is diffused over the course of the presentation, and (ii) at least one of the color and intensity of at least one of said plurality of light emitting diodes, to produce a desired presentation over a set period.

19. An electrically operated diffuser according to claim 13, further comprising an acoustical generator for generating sounds.

20. An electrically operated diffuser according to claim 19, further comprising (i) a memory for storing at least one audio file and (ii) a processor for causing said acoustical generator to generate sounds in accordance with the at least one audio file.

21. An electrically operated diffuser according to claim 20, wherein said processor is programmable so as to allow a user to control said acoustical generator, said light controller, and said fragrance controller to produce a predetermined presentation over a set period of time.

22. An electrically operated diffuser according to claim 1, further comprising a fragrance controller for adjusting the rate at which the active material is diffused.

23. An electrically operated diffuser according to claim 1, further comprising an acoustical generator for generating sounds.

24. An electrically operated diffuser according to claim 1, said at least one light emitting diode being positioned at a back surface of the compartment of said housing, such that when the active material is received in the compartment said at least one light emitting diode shines through the active material.

25. An electrically operated diffuser according to claim 24, said at least one light emitting diode being recessed in said housing to accommodate the active material in the compartment.

26. An electrically operated diffuser according to claim 24, said at least one light emitting diode comprising a plurality of light emitting diodes.

27. An electrically operated diffuser according to claim 26, wherein said plurality of light emitting diodes comprises light emitting diodes of at least two different colors.

28. An electrically operated diffuser according to claim 26, further comprising a light controller for controlling the operation of said plurality of light emitting diodes to vary at least one of the color and intensity of at least one of said plurality of light emitting diodes.

29. An electrically operated diffuser according to claim 1, further comprising a remote-use assembly, said remote-use assembly comprising a support member that supports the diffuser on a support surface remote from a wall socket and a cord that supplies power to said plug of the diffuser from the wall socket.

30. An electrically operated diffuser according to claim 29, said support member comprising a docking station that releasably holds the diffuser during use, wherein said cord transmits electrical energy from the wall socket to said docking station to power the diffuser.

31. An electrically operated diffuser according to claim 30, said docking station comprising (i) a cradle for receiving and supporting the diffuser during use and (ii) an electrical receptacle, electrically connected to said cord, for receiving said plug of the diffuser and supplying power to the diffuser from said cord.

32. An electrically operated diffuser according to claim 31, said remote-use assembly further comprising a transformer/rectifier for converting alternating current from the wall socket to direct current, said cord transmitting the direct current to said receptacle to power the diffuser.

33. An electrically operated diffuser according to claim 29, said at least one light emitting diode shining through at least one window in said housing to project an image in the shape of said at least one window onto a surface.

34. An electrically operated diffuser according to claim 33, further comprising a light controller for controlling the operation of said plurality of light emitting diodes.

35. An electrically operated diffuser according to claim 1, said at least one light emitting diode shining through at least one window in said housing to project an image in the shape of said at least one window onto a surface.

36. An electrically operated diffuser according to claim 35, further comprising a light controller for controlling the operation of said plurality of light emitting diodes.

37. An electrically operated diffuser according to claim 1, further comprising at least one sensor chosen from the group consisting of light sensors, temperature sensors, sound sensors, movement sensors, and fragrance sensors.

38. An electrically operated diffuser, comprising:
a housing having a compartment for receiving an active material;
a plug disposed on said housing for connection of the diffuser to a power source;
a heating element located in proximity to the compartment of said housing, to heat an active material received in the compartment; and
at least one light emitting diode disposed in said housing and serving as a nightlight, said at least one light emitting diode having a luminous intensity rating of at least about 5000 mcd at 20 mA,
wherein said heating element and said at least one light emitting diode are electrically connected to said plug, said at least one light emitting diode being electrically connected to said plug via a full-wave bridge circuit,
wherein when activated, said at least one light emitting diode provides minimal heat to said active material, and
wherein a combined power consumption of said heating element and said at least one light emitting diode is at most two watts.

39. An electrically operated diffuser system according to claim 38, further comprising an actuator switch for selectively activating said at least one light emitting diode to illuminate.

40. An electrically operated diffuser system according to claim 38, wherein said active material is contained in a replaceable cartridge.

41. An electrically operated diffuser system according to claim 40, wherein said active material is an air freshener material.

42. An electrically operated diffuser system according to claim 38, wherein said at least one light emitting diode serves as a nightlight.

43. An electrically operated diffuser system according to claim 38, wherein said at least one light emitting diode comprises a plurality of light emitting diodes.

44. An electrically operated diffuser according to claim 43, wherein said plurality of light emitting diodes comprises light emitting diodes of at least two different colors.

45. An electrically operated diffuser according to claim 44, further comprising a light controller for controlling the operation of said plurality of light emitting diodes.

46. An electrically operated diffuser according to claim 45, further comprising a processor for controlling the operation of said light controller to produce a predetermined presentation.

47. An electrically operated diffuser according to claim 38, further comprising at least one sensor chosen from the group consisting of light sensors, temperature sensors, sound sensors, movement sensors, and fragrance sensors.

48. An electrically operated diffuser, comprising:
a housing having a compartment for receiving an active material;
a heating element located in proximity to the compartment of said housing, to heat an active material received in the compartment; and
at least one light emitting diode disposed in said housing and being positioned at a back surface of the compartment of said housing, such that when the active material is received in the compartment said at least one light emitting diode shines through the active material, and
wherein a combined power consumption of said heating element and said at least one light emitting diode is at most two watts.

49. An electrically operated diffuser according to claim 48, wherein said at least one light emitting diode comprises a plurality of light emitting diodes.

50. An electrically operated diffuser according to claim 49, wherein said plurality of light emitting diodes comprises light emitting diodes of at least two different colors.

51. An electrically operated diffuser according to claim 50, further comprising a light controller for controlling the operation of said plurality of light emitting diodes.

52. An electrically operated diffuser according to claim 48, further comprising at least one sensor chosen from the group consisting of light sensors, temperature sensors, sound sensors, movement sensors, and fragrance sensors.

* * * * *